(12) United States Patent
Abel

(10) Patent No.: US 9,629,824 B2
(45) Date of Patent: Apr. 25, 2017

(54) INDOLE DERIVATIVES AND PROCESS FOR THEIR PREPARATION

(71) Applicant: Ramot at Tel-Aviv University Ltd., Tel-Aviv (IL)

(72) Inventor: Ulrich Abel, Bad Homburg (DE)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 15/095,188

(22) Filed: Apr. 11, 2016

(65) Prior Publication Data

US 2016/0220535 A1 Aug. 4, 2016

Related U.S. Application Data

(63) Continuation of application No. 13/881,626, filed as application No. PCT/EP2011/068820 on Oct. 27, 2011, now Pat. No. 9,309,196.

(60) Provisional application No. 61/407,924, filed on Oct. 29, 2010.

(30) Foreign Application Priority Data

Oct. 29, 2010 (EP) .................................... 10189377

(51) Int. Cl.
| | | |
|---|---|---|
| *A61K 31/40* | (2006.01) | |
| *A61K 31/4045* | (2006.01) | |
| *C07D 209/20* | (2006.01) | |
| *C07D 405/06* | (2006.01) | |
| *A61K 31/405* | (2006.01) | |

(52) U.S. Cl.
CPC ........ *A61K 31/4045* (2013.01); *A61K 31/405* (2013.01); *C07D 209/20* (2013.01); *C07D 405/06* (2013.01)

(58) Field of Classification Search
CPC .......................... A61K 31/4045; C07D 405/06
See application file for complete search history.

(56) References Cited

U.S. PATENT DOCUMENTS

2013/0289090 A1  10/2013 Abel

FOREIGN PATENT DOCUMENTS

| WO | WO 88/03927 | 6/1988 |
|---|---|---|
| WO | WO 03/063760 | 8/2003 |
| WO | WO 03/077869 | 9/2003 |
| WO | WO 2005/000193 | 1/2005 |
| WO | WO 2005/060283 | 6/2005 |
| WO | WO 2005/060683 | 7/2005 |
| WO | WO 2009/024346 | 2/2009 |
| WO | WO 2012/055945 | 5/2012 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/indexhtml>.*
Advisory Action Before the filing of an Appeal Brief Dated Nov. 3, 2015 From the US Patent and Trademark Office Re. U.S. Appl. No. 13/881,626.
Communication Pursuant to Article 94(3) EPC Dated Feb. 28, 2014 from the European Patent Office Re. Application No. 11779145.9.
European Search Report and the European Search Opinion Dated Apr. 8, 2011 from the European Patent Office Re. Application No. 10189377.4.
International Preliminary Report on Patentability Dated May 10, 2013 from the International Bureau of WIPO Re. Application No. PCT/EP2011/068820.
International Search Report and the Written Opinion Dated Dec. 1, 2011 from the International Searching Authority Re. Application No. PCT/EP2011/068820.
Notification of Reasons of Rejection Dated Jun. 30, 2015 from the Japanese Patent Office Re. Application No. 2013-535428 and Its Translation Into English.
Official Action Dated Nov. 6, 2014 from the US Patent and Trademark Office Re. U.S. Appl. No. 13/881,626.
Official Action Dated Aug. 20, 2015 from the US Patent and Trademark Office Re. U.S. Appl. No. 13/881,626.

(Continued)

*Primary Examiner* — Shawquia Jackson

(57) ABSTRACT

Substituted indole derivatives of formula (I)

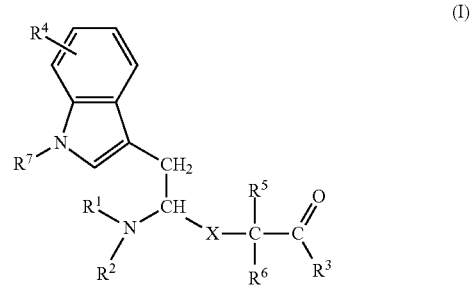

wherein the radicals have e.g. the following meaning:
$R^1$ is hydrogen, —$C_{1-6}$-alkyl, $R^2$ is hydrogen, —$C_{1-6}$-alkyl or cyclo$C_{3-12}$-alkyl;
$R^3$ is —OR
$R^4$ is hydrogen or halogen,
$R^5$ is hydrogen, —$C_{1-6}$-alkyl
$R^6$ is hydrogen, —$C_{1-6}$-alkyl
R is hydrogen or —$C_{1-6}$-alkyl;
X is a group —C(O)$CH_2$— or —CH═CH—;
$R^7$ is hydrogen
are potent inhibitors of Abeta peptide polymerization and can be used for the treatment of e.g. Alzheimers disease or ocular disorders.

9 Claims, No Drawings

(56) References Cited

OTHER PUBLICATIONS

Garcia-Lopez et al. "Synthesis and Inhibitory Activities Against Aminopeptidase B and Enkephalin-Degrading Enzymes of Ketomethylene Dipeptide Analogues of Arphamenines", Archiv der Pharmazie, XP002630632, 325(1): 3-8, 1992. H—(S) Trp-Phi-(Co—CH2)—(R,S)Orn-OH, H—(S) Trp-Phi-(CO—CH2)-(R,S)Lys-OH, P.3, Compounds 6, 7, Use as Aminopeptidase and Enkephalin-Degrading Enzyme Inhbitors.

Garcia-Lopez et al. "Synthesis of Ketomethylene Dipeptides Containing Basic Amino Acid Analogues at C-Terminus", Tetrahedron, XP002630633, 44(16): 5131-5138, 1988. H—(S)Trp-Phi-(CO—CH2)—(R,S)Orn-OH, H—(S)Trp-Phi-(CO—CH2)-(R,S)Lys-OH, Compounds 6b, 12b.

Hudspeth et al. "Preparation of Peptides as Renin Inhibitors", HCAPLUS Database [Online], ACS on STN, Accession No. 1989:439861, Database Document No. 111:39861, Aug. 5, 1989.

Kornberg et al. "Synthesis of TRP-VAL Non-Cleavable Dipeptide Transition State Isosteres", Bioorganic & Medicinal Chemistry Letters, XP026679592, 3(6): 1257-1262, Jun. 1, 1993. Delta-[[(1,1-Dimethylethoxy)Carbonyl]Amino]-Gamma-Hydroxy-Alpha-(1-Methylethyl)-(1H)-Indole-3-Hexanoic Acid 1,1-Dimethylethyl Ester, P.1259, Compound 6.

Kornberg et al. "Synthesis of Trp-Val Non-Cleavable Dipeptide Transition State Isosteres", HCAPLUS Database [Online], ACS on STN, Accession No. 1994:8954, Database Document No. 120:8954, Jan. 8, 1994.

Shue et al. "Double Bond Isosteres of the Peptide Bond: Synthesis and Biological Activity of Cholecystokinin (CCK) C-Terminal Hexapeptide Analogs", Bioorganic & Medicinal Chemistry, XP026608894, 1(3): 161-171, Sep. 1, 1993. 2-Butyl-5-[[(1,1-Dimethylethoxy)Carbonyl]Amino]-6-(1H-Indol-3-Y1)-3-Hexenoic Acid, Table 1, Compound 1c, Synthesis Scheme 1, P.161, 1-h Col., Line 4, Pam 1-Line 5, Mode of Action is Cholecystokinin Recepor, P.162 Use in Therapy of Anxiety, for Analgesia and to Enhance Cognitive Functions.

\* cited by examiner

INDOLE DERIVATIVES AND PROCESS FOR THEIR PREPARATION

RELATED APPLICATIONS

This application is a continuation of U.S. patent application Ser. No. 13/881,626 filed on Jul. 19, 2013, which is a National Phase of PCT Patent Application No. PCT/EP2011/068820 filed on Oct. 27, 2011, which claims the benefit of priority of U.S. Provisional Patent Application No. 61/407,924 filed on Oct. 29, 2010 and of European Patent Application No. 10189377.4 filed on Oct. 29, 2010.

The contents of the above applications are all incorporated by reference as if fully set forth herein in their entirety.

The present invention relates to indole derivatives, which can act as modulators of the aggregation and/or polymerization of β-amyloid peptides (Abeta peptides). The invention also is directed to methods for the preparation of indole derivatives and their use as a medicament for the treatment and/or prevention of various diseases and disorders. The compounds can e. g. be used against neurological diseases and ocular disorders.

The present invention in particular relates to the prevention and treatment of CNS-related diseases and ocular disorders, in particular of glaucoma. The compounds can act through blocking the negative effects of Abeta peptides. The invention also relates to pharmaceutical compositions for effecting such prevention and treatment.

FIELD AND BACKGROUND OF THE INVENTION

The treatment of CNS diseases and ocular disorders are worldwide important fields of research. Several heterocyclic compounds have shown to interact with neurotransmitters which are released by neurons of the central nervous system (CNS). Some compounds have been tested for the treatment of CNS-disorders such as Alzheimers disease. Scientific studies have also shown that glaucoma is a leading cause of blindness. One pathologic sign of glaucoma is the progressive degeneration of retinal ganglion cells and their axons which form the optic nerve. The classification of glaucoma also includes the following types:

Primary angle-closure glaucoma, secondary open-angle glaucoma, steroid-induced glaucoma, traumatic glaucoma, pigmentary dispersion syndrome, pseudo-exfoliation syndrome, secondary angle-closure glaucoma, neovascular glaucoma, uveitis and glaucoma and other non further specified eye pathologies.

In addition, age-related macular degeneration is a typical condition which has features of glaucoma and leads to a progressive loss of vision, leading finally to blindness. The treatment of ocular diseases includes the treatment of elevation in the intraocular pressure (IOP) over a normal range. Many individuals with clearly have elevated IOP do not develop glaucoma, and many patients with glaucoma do not have an increased IOP.

Currently available medications/drug compounds for the treatment of ocular diseases, in particular glaucoma, belong to several pharmacological classes, including β-adrenergic blockers, cholinergic agonists, carbonic anhydrase inhibitors and alpha agonists. All of them operate under a mechanism whereby the IOP is lowered. These existing medications are typically administered locally, e.g. as eye drops. Hyperosmotics may also be administered intravenously for emergency treatment. In addition, laser therapy and surgical approaches are applied in special cases of ocular diseases.

There is however an unmet medical need for better pharmaceutical drug compounds and alternative treatment strategies. Particularly for patients with progressive glaucomatous damage under normalized IOP, a drug therapy focusing on the rescue of degenerating retinal ganglion cells is needed. A particular need is for stable drug compounds which easily can be applied to humans and other mammals.

There are different scientific theories regarding the causes for the degeneration of the retinal ganglion cells including mechanical, vascular and excitotoxic mechanisms. The β-amyloid peptide has been found to co-localize with dying retinal ganglion cells [see Yoneda S, "Vitreous fluid levels of beta-amyloid (1-42) and tau in patients with retinal diseases", Jpn. J. Ophthalmol. 2005, 49(2) p.106-108]. Furthermore, animal studies demonstrated that the soluble $A\beta_{1-42}$ peptide oligomers are potent toxins for retinal ganglion cells [see Guo L, "Targeting amyloid-β in glaucoma treatment", PNAS 2007, 104(33), p.13444-13449]. This study of L. Guo showed that inhibition of aggregation of Abeta reduces glaucomatous degeneration of retinal ganglion cells. The inhibitors used in the animal experiments were known compounds, such as the diazo-biphenyl-derivative Congo red and Abeta antibodies. These agents however are pharmacological research tools only. Abeta antibodies are known to block Abeta aggregation specifically, however the usefulness of anti-Abeta antibodies for the treatment of glaucoma in humans is limited by known side effects.

Some β-Secretase inhibitors can have beneficial effects on Abeta-related neurotoxicity, however the observed effects in rat retinal ganglion cells were not significant. In the literature, various types of substituted indole compounds have been disclosed which have interesting pharmaceutical properties. Some known peptidic indole derivatives can be used for pharmaceutical purposes, such as the treatment of diabetes, Alzheimers disease and others [see e.g. WO2005/000193 and WO2009/024346]. Also, neuro-protective pharmaceutical compositions have been described [see WO2003/063760 and WO2003/077869]. Several compounds that inhibit Abeta polymerization and which are effective in animal models are described in the scientific literature, e. g. cyclohexanehexol compounds [see J. Mc Laurin, Nature Medicine 12(7), 2006, p. 801-808].

Solutions of the phenolic yellow curry pigment curcumin were found to inhibit Abeta aggregation in vitro [see F. Yang, Journal of Biological Chemistry 208(7), 2005, p. 5892-5901].

However, the substances described in the prior art, are often not sufficiently active in inhibiting Abeta aggregation and/or polymerization or they have unwanted side-effects.

In the publication of Y. K. Shue, "Double bond isosteres of the peptide bond: Synthesis and biological activity of cholecystokinin (CCK) C-terminal hexapeptide analogs" (Bioorganics & Medicinal Chemistry 1, No. 3, 1993, 161-179) several indol compounds are described, which can be used for this synthesis of tetra-peptides.

As one compound, the structure (D1) is shown.

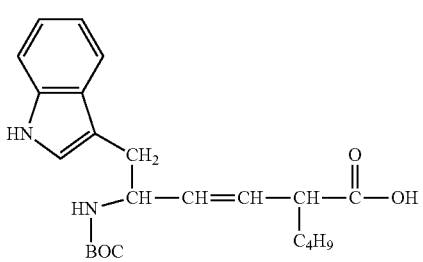
(D1)

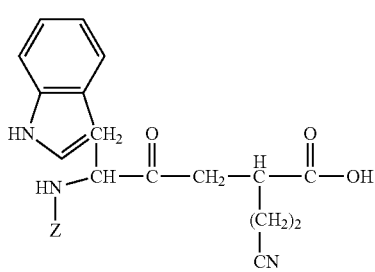
(D4)

In the publication of B. E. Kornberg "Synthesis of TRP-VAL non-cleavable dipeptide transition state isosteres" (Bioorganics & Medicinal Chemistry 3, No. 6, 1993, 1257-1262), a multiple step preparation is described. In this article, the following reaction is shown to lead to the structure (D2).

In the international patent application WO 1988/03927 various types of Renin-inhibitory peptides are disclosed, which as one amino acid can comprise L-tryptophan. In the document WO 2005/060683, several types of small peptides are described which can be useful for the treatment of Alzheimers disease. Several of the peptides disclosed can comprise a tryptophan structure.

SUMMARY OF THE INVENTION

It now has been found that certain indole derivatives which differ in structure from the compounds described in the prior art can interact with neurotransmitters in the central nervous system. The compounds also are potent inhibitors of the Abeta aggregation and/or polymerization. Therefore, these indole derivatives can be therapeutically beneficial in the treatment of conditions which involve abnormal Abeta polymerization or in which modulation of Abeta polymerization results in therapeutic benefit, such as CNS and ocular disorders and diseases.

The invention in particular relates to an indole compound of formula (I)

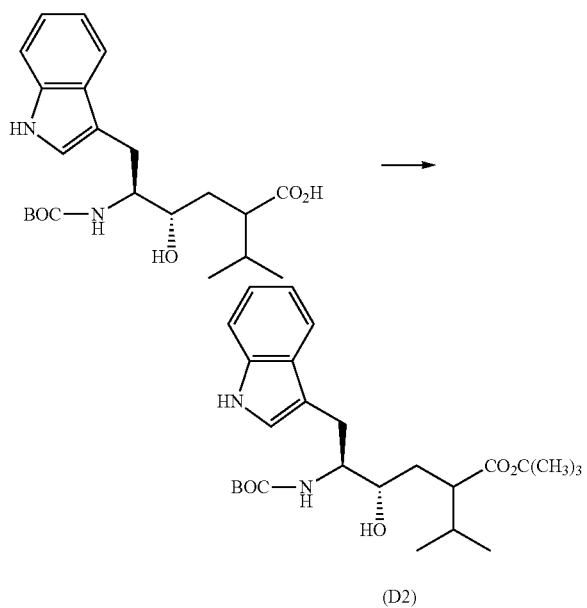

(D2)

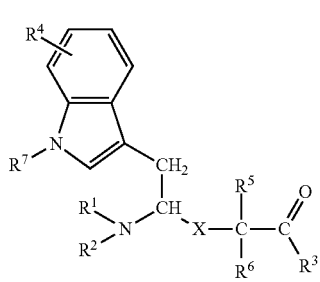

(I)

In the publication of Maria Teresa Garcia-Lopez "Synthesis and Inhibitory Activities against Aminopeptidase B and Enkephalin-Degrading Enzymes of Ketomethylene Dipeptide Analogues of Arphamenines" (Archiv der Pharmazie, 325, No. 1, 1992, 3-8) various dipeptide compounds are described which have inhibitory activities against Aminopeptidase B.

In the publication of Maria Teresa Garcia-Lopez "Synthesis of ketomethylene dipeptides containing basic amino acid analogues at C-terminus" (Tetrahedron, 44, No. 16, 1988, 1531-1538) several indol-derivatives are described such as the following compound (D4).

wherein
$R^1$ is hydrogen, —$C_{1-6}$-alkyl, cyclo$C_{3-12}$-alkyl, —C(O)—R or —C(O)OR;
$R^2$ is hydrogen, —$C_{1-6}$-alkyl or cyclo$C_{3-12}$-alkyl;
$R^3$ is —OR, —NHR or —$NR_2$;
$R^4$ is hydrogen, halogen, cyano, trifluoromethyl, —$C_{1-6}$-alkyl, —$C_{6-10}$-aryl, heteroaryl, —OR, —NHR, —NRR, —C(O)—R or —C(O)—NHR;
$R^5$ is hydrogen, —$C_{1-6}$-alkyl or $C_{2-6}$-alkenyl; or
$R^5$ and $R^6$ together with the carbon atom carrying them form a cyclic system with 3 to 6 carbon atoms;
$R^6$ is hydrogen, —$C_{1-6}$-alkyl or $C_{2-6}$-alkenyl;
R is hydrogen, —$C_{1-6}$-alkyl, or —$C_{6-10}$-aryl;
X is a group —C(O)$CH_2$—, —CH(OH)$CH_2$—, —CH=CH— or —$CH_2$—NH—C(O)—;
$R^7$ is hydrogen, methyl, ethyl, propyl or cyclopropyl
or an optical isomer, pharmaceutically acceptable salt, hydrate, solvate, or polymorph thereof.

The present invention also includes all optical isomers, pharmaceutically acceptable salts, hydrates, solvates and polymorphs of the compounds of formula (I). The invention also relates to analogs and derivatives of compounds of formula (I).

The two substituents $R^5$ and $R^6$ can, together with the carbon atom carrying them, form a cyclic system with 3 to 6 carbon atoms. This cyclic system can also contain one ring element from the group —O—, —S— or —NH—. Typical cyclic systems are e.g. cyclohexane, cyclopentane, cyclobutane, cyclopropane, oxetane and acetidine rings.

The groups $R^1$, $R^2$ and $R^3$ often denote independently of each other, hydrogen or $C_{1-3}$-alkyl. The term "$C_{1-6}$-alkyl" represents straight or branched chain alkyl groups such as methyl, ethyl, n-propyl, 2-propyl, n-butyl and tert-butyl.

The alkyl group may in one embodiment of the invention be optionally substituted by one to five substituents selected from halogen, amino or hydroxyl, or the group —$CF_3$.

The term "$C_{2-6}$-alkenyl" represents straight or branched chain alkenyl groups.

The term "cyclo$C_{3-12}$-alkyl" represents monocyclic or bicyclic, alkyl groups, including cyclopropyl, cyclobutyl, cyclopentyl, cyclohexyl. The cycloalkyl groups in one embodiment of the invention may be optionally substituted by one to five substituents selected from halogen, amino or hydroxyl.

The term "$C_{6-10}$-aryl" represents phenyl or naphthyl, wherein the phenyl or naphthyl group may in one embodiment of the invention be optionally substituted by one to five substituents selected from halogen, amino or hydroxyl.

The term "heteroaryl" represents an aromatic 5-6 membered ring containing from one to four heteroatoms selected from oxygen, sulfur and nitrogen, or a bicyclic group comprising a 5-6 membered ring containing from one to four heteroatoms selected from oxygen, sulfur and nitrogen fused with a benzene ring or a 5-6 membered ring containing from one to four heteroatoms selected from oxygen, sulfur and nitrogen, wherein the heteroaryl group in one embodiment of the invention may be optionally substituted by one or two substituents selected from halogen, amino or hydroxyl.

The term "halogen" represents fluorine, chlorine, bromine and iodine.

The term "analog" or "derivative" is used herein in the conventional pharmaceutical sense, to refer to a molecule that structurally resembles a reference molecule, but has been modified in a targeted and controlled manner to replace one or more specific substituents of the referent molecule with an alternate substituent, thereby generating a molecule which is structurally similar to the reference molecule. Synthesis and screening of analogs (e.g. using structural or biochemical analysis) to identify slightly modified versions of a known compound which may have improved properties (e.g. higher potency and/or selectivity at a specific targeted receptor type, greater ability to penetrate into the eye, fewer side effects) is a typical drug design approach.

The invention also relates to a compound of formula (I), wherein $R^1$ is hydrogen, —$C_{1-6}$-alkyl, —C(O)—R or —C(O)—OR;

$R^2$ is hydrogen or —$C_{1-6}$-alkyl;

$R^3$ is —OR, —NHR or —$NR_2$;

$R^4$ is hydrogen, halogen, cyano, trifluoromethyl, —$C_{1-6}$-alkyl;

$R^5$ is hydrogen or —$C_{1-6}$-alkyl; in particular —$C_{1-3}$-alkyl;

$R^6$ is hydrogen or —$C_{1-6}$-alkyl; in particular —$C_{1-3}$-alkyl; or $R^5$ and $R^6$ together with the carbon atom carrying them form a cyclic system with 3 to 6 carbon atoms;

R is hydrogen or —$C_{1-6}$-alkyl; in particular hydrogen or —$C_{1-3}$-alkyl;

X is a group —C(O)$CH_2$—, —CH(OH)$CH_2$—, —CH=CH— or —$CH_2$NHC(O)—;

$R^7$ is hydrogen or methyl;

or an optical isomer, pharmaceutically acceptable salt, hydrate, solvate, or polymorph thereof.

The invention also relates to a compound of formula (I), wherein $R^1$ is hydrogen, —$C_{1-3}$-alkyl, or —C(O)—$CH_3$;

$R^2$ is hydrogen or —$C_{1-3}$-alkyl;

$R^3$ is —OR, —NHR or —$NR_2$;

$R^4$ is hydrogen or halogen;

$R^5$ is —$C_{1-3}$-alkyl;

$R^6$ is —$C_{1-3}$-alkyl;

R is hydrogen or —$C_{1-3}$-alkyl;

X is a group —C(O)$CH_2$—, —CH(OH)$CH_2$—, —CH=CH— or —$CH_2$NHC(O)—;

$R^7$ is hydrogen;

or an optical isomer, pharmaceutically acceptable salt, hydrate, solvate, or polymorph thereof.

The invention also relates to a compound of formula (I), wherein $R^1$ is hydrogen, —$C_{1-3}$-alkyl, or —C(O)—$CH_3$;

$R^2$ is hydrogen;

$R^3$ is —OR —NHR;

$R^4$ is hydrogen;

$R^5$ is hydrogen or —$C_{1-3}$-alkyl;

$R^6$ is hydrogen or —$C_{1-3}$-alkyl;

R is hydrogen or —$C_{1-3}$-alkyl;

X is a group —C(O)$CH_2$—, —CH(OH)$CH_2$—, —CH=CH— or —$CH_2$NHC(O)—;

$R^7$ is hydrogen;

or an optical isomer, pharmaceutically acceptable salt, hydrate, solvate, or polymorph thereof.

The invention also relates to a compound of formula (I), wherein $R^1$ is hydrogen or —C(O)—$CH_3$;

$R^2$ is hydrogen;

$R^3$ is —OR —NHR;

$R^4$ is hydrogen;

$R^5$ is —$C_{1-3}$-alkyl;

$R^6$ is —$C_{1-3}$-alkyl;

R is hydrogen or —$C_{1-3}$-alkyl;

X is a group —C(O)$CH_2$—, —CH(OH)$CH_2$—, —CH=CH— or —$CH_2$NHC(O)—;

$R^7$ is hydrogen;

or an optical isomer, pharmaceutically acceptable salt, hydrate, solvate, or polymorph thereof.

In the compounds of formula (I)

the group $R^1$ often denotes hydrogen or —C(O)—CH$_3$.
the group $R^2$ often denotes hydrogen.
the group $R^3$ often denotes —OH, —OCH$_3$ or —NH—CH$_3$.
the group $R^4$ often denotes hydrogen.
the groups $R^5$ and $R^6$ often are identical, in particular they denote —CH$_3$.
the group X represents —C(O)CH$_2$— or —CH(OH)CH$_2$— or —CH═CH— or —CH$_2$NHC(O)— (the orientation of the group X being as indicated, the left side connected with the amino-group carrying chiral carbon atom).

The invention also relates to a compound of formula (I), wherein the group X represents —C(O)CH$_2$— or —CH(OH)CH$_2$— or —CH═CH— or an optical isomer, pharmaceutically acceptable salt, hydrate, solvate, or polymorph thereof.

The invention also relates to a compound of formula (I), wherein the chiral center carrying the amino group and the group X has R-configuration or a pharmaceutically acceptable salt, hydrate, solvate, or polymorph thereof.

The invention also relates to a compound according to formula (I) of claim 1 and having one of the chemical names cited in the experimental part of this application or a pharmaceutically acceptable salt, hydrate, solvate, or polymorph thereof.

One further aspect of the invention are compounds of formula (I) as described above or their optical isomers, pharmaceutically acceptable salts, hydrates, solvates or polymorphs thereof for use as a medicament. The medicament can be prepared in different formulations and can be used for various therapeutical purposes.

One further aspect of the invention are compounds of formula (I) or their optical isomers, pharmaceutically acceptable salts, hydrates, solvates or polymorphs thereof for treating or preventing of CNS-disorders, in particular of Alzheimers disease.

One further aspect of the invention are compounds of formula (I) as described above or their optical isomers, pharmaceutically acceptable salts, hydrates, solvates or polymorphs thereof for treating or preventing a disorder or disease associated with an abnormal agglomeration or polymerization of Abeta peptides.

One further aspect of the invention are compounds of formula (I) or their optical isomers, pharmaceutically acceptable salts, hydrates, solvates or polymorphs thereof for treating or preventing an ocular disorder or disease, in particular glaucoma.

Another aspect of the invention are compounds of formula (I) or their optical isomers, pharmaceutically acceptable salts, hydrates, solvates or polymorphs thereof for treating or preventing a disorder or disease selected from the group consisting of:
primary angle-closure glaucoma, secondary open-angle glaucoma, wide-angle glaucoma, steroid-induced glaucoma, traumatic glaucoma, pigmentary dispersion syndrome, pseudo exfoliation syndrome, secondary angle-closure glaucoma, neovascular glaucoma, uveitis and glaucoma, age-related macular degeneration, diabetic retinopathy, degenerative optic neuropathy and other eye pathologies characterized by a progressive loss of vision.

The invention also covers a pharmaceutical composition for the treatment, wherein the condition to be treated is selected from the group consisting of primary angle-closure glaucoma, secondary open-angle glaucoma, wide-angle glaucoma, steroid-induced glaucoma, traumatic glaucoma, pigmentary dispersion syndrome, pseudo exfoliation syndrome, secondary angle-closure glaucoma, neovascular glaucoma, uveitis and glaucoma, age-related macular degeneration, diabetic retinopathy, degenerative optic neuropathy and eye pathologies characterized by a progressive loss of vision, leading finally to blindness. Such a composition can be prepared to comprise a therapeutically effective amount of a compound of formula (I) either alone or in combination with at least one additional pharmaceutical agent which is effective in treating the optical condition.

According to the present invention, the modulators of the aggregation or polymerization of β-amyloid peptides (Abeta peptides) of formula (I) can be administered to provide neuroprotection and/or disease modification also for the following acute or chronic pathological conditions or diseases:

Alzheimers disease, Creutzfeld-Jakob's syndrome/disease, bovine spongiform encephalopathy (BSE), diseases involving β-amyloid and/or tauopathy, motor neuron diseases, amyotrophic lateral sclerosis (ALS), olivoponto-cerebellar atrophy, post-operative cognitive deficit (POCD), systemic lupus erythematosus, systemic clerosis, Sjogren's syndrome, Neuronal Ceroid Lipofuscinosis, neurodegenerative cerebellar ataxias, Parkinson's disease, Parkinson's dementia, cognitive impairment, cognitive deficits in various forms of mild cognitive impairment, cognitive deficits in various forms of dementia, dementia pugilistica, vascular and frontal lobe dementia, cognitive impairment, learning impairment, eye injuries, eye diseases, eye disorders, glaucoma, retinopathy, macular degeneration, head or brain or spinal cord injuries, head or brain or spinal cord trauma, trauma, hypoglycaemia, hypoxia, perinatal hypoxia, ischaemia, convulsions, epileptic convulsions, epilepsy, temporal lobe epilepsy, myoclonic epilepsy, inner ear insult, tinnitus, L-dopa-induced dykinesias, dyskinesias, chorea, Huntington's chorea, athetosis, dystonia, stereotypy, ballism, tardive dyskinesias, tic disorder, torticollis spasmodicus, blepharospasm, focal and generalized dystonia, nystagmus, hereditary cerebellar ataxias, corticobasal degeneration, tremor, essential tremor, abuse, addiction, nicotine addiction, nicotine abuse, alcohol addiction, alcohol abuse, opiate addiction, opiate abuse, cocaine addiction, cocaine abuse, amphetamine addiction, amphetamine abuse, anxiety disorders, panic disorders, anxiety and panic disorders, social anxiety disorder (SAD), attention deficit hyperactivity disorder (ADHD), attention deficit syndrome (ADS), restless leg syndrome (RLS), hyperactivity in children, autism, dementia, dementia in Alzheimers disease, dementia in Korsakoff syndrome, Korsakoff syndrome, vascular dementia, major depressive disorder, depression, bipolar manic-depressive disorder, irritable bowel syndrome (IBS), migraine, multiple sclerosis (MS), muscle spasms, pain, chronic pain, acute pain, inflammatory pain, schizophrenia, spasticity, Tourette's syndrome, sleep disorders, anxiety disorder, obsessive-compulsive disorder, panic disorder, posttraumatic stress disorder, social phobia, phobic disorders and schizophreniform disorder, down syndrome, diabetis mellitus (type II), familiar amyloid polyneuropathy and cerebrat amyloid angiopathy.

Optionally, the composition may further comprise another active ingredient which is not a compound of formula (I). The invention also relates to a combination to be co-administered to the living human or animal a therapeutically effective amount of a compound (I) as described above in combination with at least one additional pharmaceutical agent which is effective in treating e. g. a CNS-disorder or an ophthalmic condition, wherein the combination of the compound (I) and the at least one additional pharmaceutical agent is effective in treating the condition.

The additional pharmaceutical substance is e.g. selected from drug compounds administered to treat or prevent a CNS-disorder (such as Alzheimers) or to treat ocular diseases. Typical combination drugs are anti-Alzheimer drugs, anti-glaucoma drugs, antibiotics, anti-inflammatory drugs, steroids, anti-allergic drugs and artificial tear fluid.

An additional embodiment of the invention is a pharmaceutical composition comprising at least two different active ingredients, where the composition contains at least one compound of formula (I) as defined above or an optical isomer, pharmaceutically acceptable salt, hydrate, solvate or polymorph thereof, and contains at least one further active ingredient, and one or several pharmaceutically acceptable excipients. The two active ingredients (drug compounds) can in principal be administered together or separately. Such a further additional active ingredient (drug compound) is e. g. selected from:

acetazolamide, diclofenamide, carteolol, timolol, metipranolol, betaxolol, pindolol, levobundolol, brimonidine, clonidine, pilocarpine, carbachol, dipivefrine, apraclonidine, brinzolamide, dorzolaminde, bimatroprost, travaprost, latanoprost, chlortetracycline, ciprofloxacine, ofloxacine, fusidinic acid, gentamicine, kanamycine, levofloxacine, lomefloxacine, oxytetracycline, natamycine, azidamfenicole, chloramphenicole, tobramycine, erythromycine, polymyxin-B, acaclovir, trifluridine, betamethasone, dexamethasone, fluorometholone, hydrocortisone, prednisolone, rimexolone, cromoglicate, azelastine, lodoxamide, emedastine, nedocromile, levocabstine, olopatadinea, ketoifene, hyaluronate, dexpanthenole, tetryzoline, troxerutine, tramazoline, naphazoline, xylometazoline, phenylephrine and antazoline.

For CNS-application, the additional drug compound is e.g. selected from memantine, galantamine, donepezile and rivastigmine. Of particular interest are combinations of a compound of formula (I) with memantine.

The compound of formula (I) or the combination product is e.g. administered once a day, twice a day or three times a day. Often it is administered chronically. In one embodiment, the composition is administered in the form of eye drops, eye creams, and intraocular depot formulations. The composition can also be administered in an immediate or modified release formulation. The compound of formula (I) and the additional pharmaceutical agent can be administered separately or conjointly.

These compounds of formula (I) are preferably administered in the form of a pharmaceutical composition, which is easily to ply to a person or animal, wherein the compounds of formula (I) are present together with one or several pharmaceutically acceptable diluents, carriers, or excipients.

It is one further aspect of the invention, to provide a pharmaceutical composition comprising as active ingredient at least one compound of formula (I) as defined above or an optical isomer, pharmaceutically acceptable salt, hydrate, solvate or polymorph thereof, together with one or several pharmaceutically acceptable excipients.

It is a further object of the invention to provide a novel method of treating, eliminating, alleviating, palliating, or ameliorating undesirable CNS disorders which involve modulation of Abeta polymerization by employing a compound of formula (I) or a pharmaceutical composition containing the same.

An additional object of the invention is the provision of processes for preparing the indole derivatives. The invention therefore relates to a process for the preparation of a compound of formula (I),

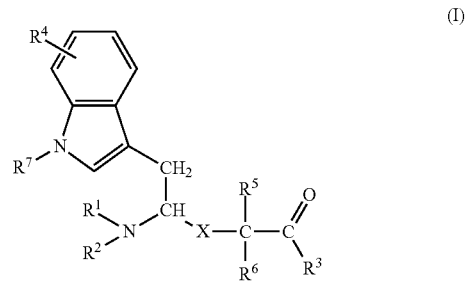

wherein
$R^1$ is hydrogen, —$C_{1-6}$-alkyl, cyclo$C_{3-12}$-alkyl, —C(O)—R or —C(S)—R;
$R^2$ is hydrogen, —$C_{1-6}$-alkyl or cyclo$C_{3-12}$-alkyl;
$R^3$ is —OR, —NHR or —$NR_2$;
$R^4$ is hydrogen, halogen, cyano, trifluoromethyl, nitro, —$C_{1-6}$-alkyl, —$C_{6-10}$-aryl, heteroaryl, —OR, —NHR, —NRR, —C(O)—R or —C(O)—NHR;
$R^5$ is hydrogen, —$C_{1-6}$-alkyl or $C_{2-6}$-alkenyl;
$R^6$ is hydrogen, —$C_{1-6}$-alkyl or $C_{2-6}$-alkenyl; or
$R^5$ and $R^6$ together with the carbon atom carrying them form a cyclid system with 3 to 6 carbon atoms;
R is hydrogen or —$C_{1-6}$-alkyl;
X is a group —C(O)$CH_2$—, —CH(OH)$CH_2$—, —CH=CH— or —$CH_2$—NH—C(O)—;
$R^7$ is hydrogen, methyl, ethyl, propyl or cyclopropyl;
comprising the step of starting from an intermediate a compound of formula (II)

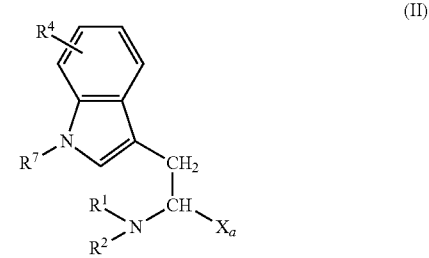

wherein
$X_a$ is a carbonyl function carrying group, such as —CHO, and the other radicals are defined as above,
which then is transformed in one ore several steps, preferably in the presence of a condensing agent, to yield a compound of formula (I), which then is converted, if desired, to a pharmaceutically acceptable salt, hydrate, solvate, or polymorph.

Furthermore, the preparation of optical isomers, pharmaceutically acceptable salts, hydrates, solvates, and polymorphs of a compounds of formula (I) is part of the invention. Also, the manufacturing or preparation of a medicament is part of the invention.

The invention also relates to compounds of the formula (I) which are marked by radioactive atoms. Typical compounds include those where one or more hydrogens are substituted by tritium, where one or more $C^{12}$ are substituted by $C^{14}$, where one or more fluor atoms are substituted by $F^{18}$ or other isotopes. These can be used for the treatment of diseases (e.g. cancer) but also for diagnostic purposes. The radioactive atoms exchanged in the molecule are often isotopes of carbon, hydrogen, halogen, sulphur or phosphor.

The invention in general relates to the use of modulators of the polymerization of Abeta peptides for the preparation of a medicament and for the treatment of various diseases as mentioned above in a mammal, including humans.

The invention also relates to an intermediate compound of formula (II)

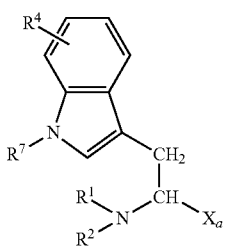

(II)

wherein $X_a$ is a carbonyl function carrying group, e.g. —CHO.

The invention also relates to a process of preparation, where the compound of formula (I) is prepared in an enantio-selective reaction, preferably leading to the R-configurated compound.

Moreover, the modulators of the polymerization of Abeta peptides of formula (I) as described above have a high activity when administered in combination with other substances exhibiting neurological effects via different mechanisms. The invention also relates to a pharmaceutical composition comprising at least two different active ingredient, containing at least one compound of formula (I) as defined above, and furthermore containing at least one NMDA-antagonist, together with one or more pharmaceutically acceptable excipients. These compositions can be used for the treatment of CNS-related diseases, cognitive enhancement and for neuro-protection. Simultaneous administration of modulators of the polymerization of Abeta peptides and NMDA receptor antagonists can provide neuroprotection in animal models.

With respect to the compounds of formula (I) as described above, the combined therapy exhibits a greater neuroprotective effect than monotherapy with either an modulator of the polymerization of Abeta peptides or an NMDA receptor antagonist. As particularly active NMDA receptor antagonist, the compound Memantine can be named, which is also known as 1-Amino-3,5-dimethyladamantane (see U.S. Pat. Nos. 4,122,193; 4,273,774; and 5,061,703).

Memantine is a systemically-active noncompetitive NMDA receptor antagonist having moderate affinity for the receptor. The combination of NMDA antagonists with modulators of formula (I) can be realized in a single pharmaceutical composition (as principally described in the prior art) comprising a compound of formula (I) of the present invention and an NMDA receptor antagonist, in one pharmaceutical formulation, or in two separate pharmaceutical compositions or formulations, one comprising a compound of formula (I) of the present invention and one comprising an NMDA receptor antagonist in a pharmaceutical formulation, to be administered conjointly (simultaneously or sequentially). For the sequential administration to be considered "conjoint", however, the compound of formula (I) of the present invention and the NMDA receptor antagonist must be administered separated by a time interval that still permits the resultant beneficial effect in a mammal. For example, the compound of formula (I) and the NMDA receptor antagonist must be administered on the same day (e.g., each—once or twice daily), preferably within an hour of each other, and most preferably simultaneously.

The following Scheme describes the preparation of compounds of formula (I) of the present invention. All of the starting materials may be prepared by procedures described in these schemes, by procedures well known to one of ordinary skill in organic chemistry, or may be obtained commercially. All of the final compounds of the present invention may be prepared by procedures described in these charts or by procedures analogous thereto, which would be well known to one of ordinary skill in organic chemistry. All of the variables used in the schemes are as defined below or as in the claims. The compounds containing one or more chiral centers can be prepared as racemates or mixtures of various stereoisomers and then separated. However, they also can be prepared by a special enantioselective synthesis. For several of the chiral compounds, the enantiomers differ in pharmacological activity.

The indole compounds of the present invention may be synthesized by different synthetic routes by using reactions principally known to the skilled chemist.

Some preferred methods of preparation of the compounds of formula (I)

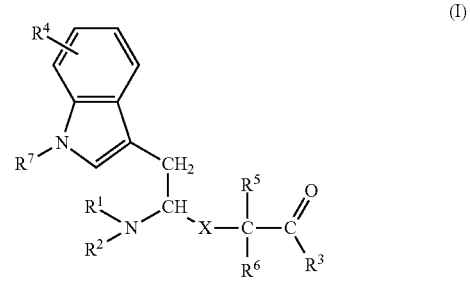

(I)

depending on whether the spacer element X is a group
—C(O)CH$_2$—,
—CH(OH)CH$_2$—, —CH=CH— or
—CH$_2$—NH—C(O)— are summarized in the following general Scheme I

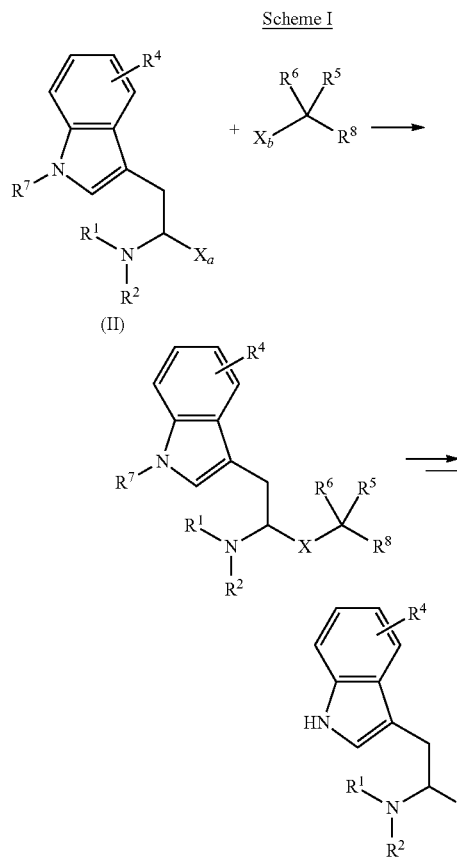

Scheme I (II)

wherein

X$_a$ is e.g. —CHO (or —CH$_2$—NH$_2$);

X$_b$ is e.g. (Ph)$_2$P(O)CH$_2$—, with Ph being Phenyl, (or —COOH);

R$^8$ is e.g. —CH$_2$O-TBS or CH$_2$O—Si(alkyl)$_3$, with TBS being tributylsilyl, (or —COOCH$_3$).

Scheme II shows a method for preparing compounds of the type of examples 6 to 14.

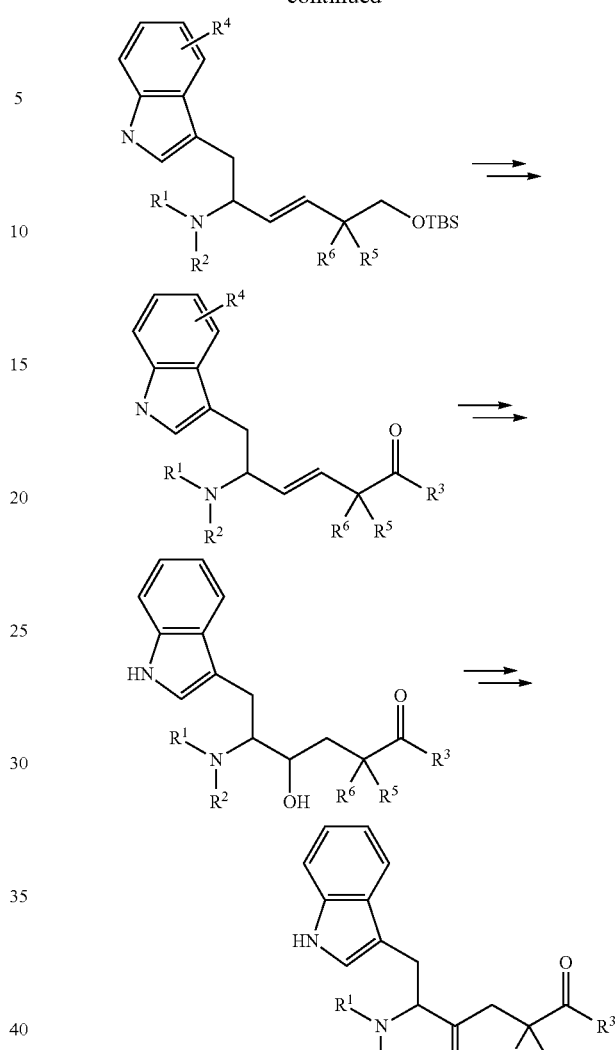

Scheme III shows a method for preparing compounds of the type of example 1.

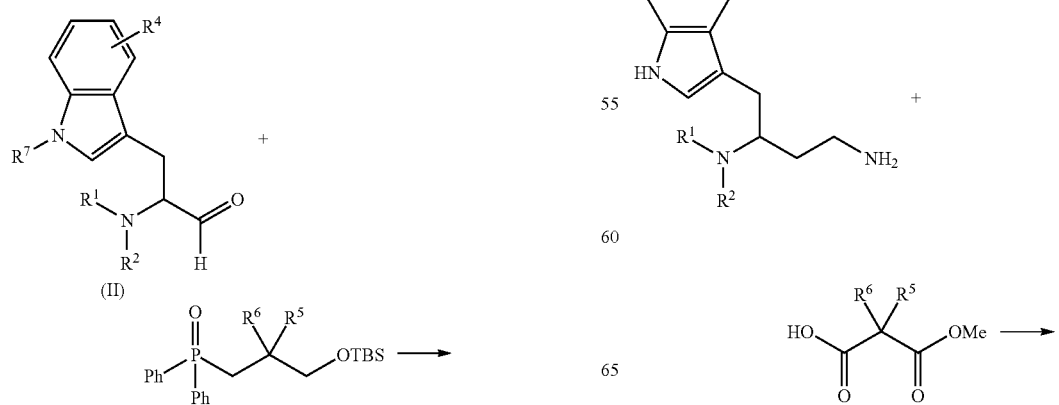

-continued

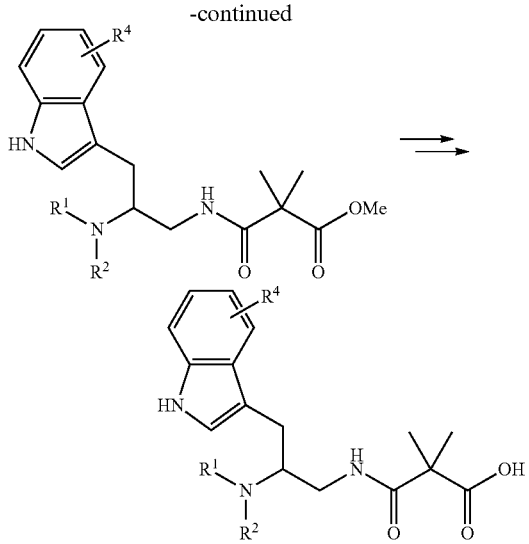

The pure stereoisomeric forms (and in particular optical isomers) of the compounds and the intermediates of this invention may be obtained by the application of art-known procedures. Diastereomers may be separated by physical separation methods such as selective crystallization and chromatographic techniques, e.g. liquid chromatography using chiral stationary phases. Enantiomers (optically active isomers) may be separated from each other by selective crystallization of their diastereomeric salts with optically active acids. Alternatively, enantiomers may be separated by chromatographic techniques using chiral stationary phases.

Said pure stereoisomeric forms may also be derived from the corresponding pure stereoisomeric form of appropriate starting materials, provided that the reaction occur stereoselectively. Stereoisomeric forms of formula (I) are included within the scope of this invention.

For therapeutic uses, the salts of the compounds of formula (I) are those wherein the counterion is pharmaceutically acceptable. However, salts of acids (and bases), which are non-pharmaceutically acceptable, may also find use, for example, in the preparation and purification of pharmaceutically acceptable compounds. All salts whether pharmaceutically acceptable or not are included in the present invention. The pharmaceutically acceptable salts as mentioned above are meant to comprise the therapeutically active non-toxic salt forms, which the compounds of formula (I) are able to form. The latter can conveniently be obtained by treating the base form with such appropriate acids as inorganic acids, e.g. hydrohalic acids such as hydrochloric, hydrobromic and the like; sulfuric acid; nitric acid; phosphoric acid and the like; or organic acids such as acetic, propanoic, hydroxyacetic, 2-hydroxypropanoic, oxo-propanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfonic, 2-hydroxybenzoic, 4-amino-2-hydroxybenzoic and the like acids. Conversely, the salt form can be converted by treatment with alkali into the free base form.

Preparation of Pharmaceutical Compositions

The active ingredients of formula (I) of the invention, together with one or more conventional excipients (adjuvants, carriers, or diluents) may be placed into the form of pharmaceutical compositions and unit dosages thereof. The compositions may be employed as solids, such as coated or uncoated tablets or filled capsules, or liquids, such as solutions, suspensions, emulsions, or capsules filled with the same. The compositions can be prepared for oral use.

They can be in the form of suppositories or capsules for rectal administration.

Compositions can be in the form of sterile injectable solutions for parenteral (including intravenous or subcutaneous) use. They can be in liquid or semi-liquid form for ophthalmic application to the eye.

Such pharmaceutical compositions and unit dosage forms thereof may comprise conventional or new ingredients in conventional or special proportions, with or without additional active compounds. Such unit dosage forms may contain any suitable effective amount of the active ingredient of formula (I) commensurate with the intended daily dosage range to be employed.

Compositions containing 0.5 to 1000 milligrams, preferably 1 to 100 milligrams of active ingredient per application unit are suitable representative unit dosage forms.

The term "excipient" applied to pharmaceutical compositions of the invention refers to a diluents, adjuvants or carrier with which an active compound of formula (I) is administered. Such pharmaceutical excipients often are sterile liquids, such as water or saline solutions. Other excipients, depending on the type of administration, can be aqueous dextrose solutions, aqueous glycerol solutions, and oils, including those of animal, vegetable or synthetic origin (see A. R. Gennaro, 20$^{th}$ Edition, "Remington: The Science and Practice of Pharmacy").

Due to their high degree of activity and their low toxicity, together presenting a favorable therapeutic index, the compounds of formula (I) may be administered to a subject, e.g., a living mammal (including a human) body, for the treatment, alleviation, or amelioration, palliation, or elimination of an indication or condition which is susceptible thereto, or representatively of an indication or condition set forth elsewhere in this application, preferably concurrently, simultaneously, or together with one or more pharmaceutically-acceptable excipients, especially in the form of a pharmaceutical composition thereof, whether by oral, rectal, parental or topical route, in an effective amount. Suitable dosage ranges are 1 to 1000 milligrams daily, preferably 5 to 500 milligrams daily, and especially 10 to 500 milligrams daily, depending as usual upon the exact mode of administration, form in which administered, the indication toward which the administration is directed, the subject involved and the body weight of the subject involved, and the preference and experience of the physician or veterinarian in charge. The term "therapeutically effective" applied to dose or amount refers to that quantity of a compound or pharmaceutical composition that is sufficient to result in a desired activity upon administration to a living animal body in need thereof.

The compounds of formula (I) of the present invention may be administered orally, topically, parenterally, or mucosally (e.g., buccally, by inhalation, or rectally) in dosage unit formulations containing conventional non-toxic pharmaceutically acceptable excipients. For ophthalmological applications (for ocular diseases and disorders), topic formulations are often applied. They are often water based solutions or dispensions.

The compound of formula (I) can also be administered orally in the form of a capsule, a tablet, or the like (see Remington: The Science and Practice of Pharmacy, 20$^{th}$ Edition). The orally administered compositions can be administered in the form of a time-controlled release vehicle, including diffusion-controlled systems, osmotic devices, dissolution-controlled matrices, and erodible/degradable matrices.

For oral administration in the form of a tablet or capsule, the compound of formula (I) may be combined with non-toxic, pharmaceutically acceptable excipients such as binding agents (e.g., pregelatinized maize starch, polyvinylpyrrolidone or hydroxypropyl methylcellulose); fillers (e.g., lactose, sucrose, glucose, mannitol, sorbitol and other reducing and non-reducing sugars, microcrystalline cellulose, calcium sulfate, or calcium hydrogen phosphate); lubricants (e.g., magnesium stearate, talc, or silica, steric acid, sodium stearyl fumarate, glyceryl behenate, calcium stearate, and the like); disintegrants (e.g., potato starch or sodium starch glycolate); or wetting agents (e.g., sodium lauryl sulphate), coloring and flavoring agents, gelatin, sweeteners, natural and synthetic gums (such as acacia, tragacanth or alginates), buffer salts, carboxymethylcellulose, polyethyleneglycol, waxes, and the like. The tablets containing a compound of formula (I) may be coated by methods well known in the art.

For oral administration in liquid form, the drug components may be combined with non-toxic, pharmaceutically acceptable inert carriers or solvents (e.g., ethanol, glycerol, water), suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), preservatives (e.g., methyl or propyl-p-hydroxybenzoates or sorbic acid), and the like. Stabilizing agents such as antioxidants (BHA, BHT, propyl gallate, sodium ascorbate, citric acid) may also be added to stabilize the dosage forms.

The compositions of the invention containing a compound of formula (I) may be also introduced in beads, microspheres or microcapsules, e.g., fabricated from polyglycolic acid/lactic acid (PGLA). Liquid preparations for oral administration may take the form of solutions, syrups, emulsions or suspensions, or they may be presented as a dry product for reconstitution with water or other suitable vehicle before use. Preparations for oral administration may be suitably formulated to give controlled or postponed release of the active compound.

The active drugs of formula (I) may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines, as is well known.

The active compound of formula (I) may also be coupled with soluble polymers as targetable drug carriers. Such polymers include polyvinyl-pyrrolidone, pyran copolymer, polyhydroxy-propyl methacrylamide-phenol, polyhydroxyethyl-aspartamide-phenol, or polyethyleneoxide-polylysine substituted with palmitoyl residues. Furthermore, the compound of formula (I) may be coupled to a class of biodegradable polymers useful in achieving controlled release of a drug, for example, polylactic acid, polyglycolic acid, copolymers of polylactic and polyglycolic acid, polyepsilon caprolactone, polyhydroxybutyric acid, polyorthoesters, polyacetals, polyhydropyrans, polycyanoacrylates, and cross-linked or amphipathic block copolymers of hydrogels.

For administration by inhalation, the therapeutics according to the present invention containing as active compound a compound of formula (I) may be conveniently delivered in the form of an aerosol spray presentation from pressurized packs or a nebulizer, with the use of a suitable propellant, e.g. dichlorodifluoromethane or other suitable gas.

The formulations of the invention containing a compound of formula (I) may be delivered parenterally, i.e., by intravenous (i.v.), intracerebroventricular (i.c.v.), subcutaneous (s.c.), intraperitoneal (i.p.), intramuscular (i.m.), subdermal (s.d.), or intradermal (i.d.) administration, by direct injection, e.g. via bolus injection or continuous infusion.

Formulations for injection (in particular for application to the eye) can be presented in unit dosage form, e.g., in ampoules or in multi-dose containers, with an added preservative. The compositions can be a suspension, solutions, or emulsion e.g. in aqueous vehicles, and can contain excipients such as suspending, stabilizing and/or dispersing agents. Alternatively, the compound of formula (I) can be in powder form for reconstitution with a suitable excipient, e.g., sterile pyrogen-free water, for reconstitution.

Compositions of the present invention containing a compound of formula (I) may also be formulated for rectal administration, e.g., as suppositories or retention enemas (e.g., containing conventional suppository bases such as cocoa butter or other glycerides).

The compositions containing a compound of formula (I) may be presented in a pack or dispenser device, which may contain one or more unit dosage forms containing the active ingredient and/or may contain different dosage levels to facilitate dosage titration. The pack may comprise metal or plastic foil, such as a blister pack. The pack or dispenser device may be accompanied by instructions for administration. Compositions of the invention formulated in a compatible pharmaceutical carrier may also be prepared, placed in an appropriate container, and labeled for treatment of an indicated condition.

As disclosed herein, the dose of the components in the compositions of the present invention is determined to ensure that the dose administered continuously or intermittently will not exceed an amount determined after consideration of the results in test animals and the individual conditions of a patient. A specific dose naturally varies depending on the dosage procedure, the conditions of a patient or a subject animal such as age, body weight, sex, sensitivity, feed, dosage period, drugs used in combination, seriousness of the disease. The appropriate dose and dosing times under certain conditions can be determined by the test based on the above-described indices but may be refined and ultimately decided according to the judgment of the practitioner and each patient's circumstances (age, general condition, severity of symptoms, sex, etc.) according to standard clinical techniques.

Toxicity and therapeutic efficacy of the compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it may be expressed as the ratio $ED_{50}/LD_{50}$. Those pharmaceutical compositions that exhibit large therapeutic indices are preferred.

EXAMPLES

With the aid of commonly used solvents and excipients, the compounds of formula (I) can be brought into a liquid formulation or be processed into tablets, coated tablets, capsules, drip solutions, suppositories, injection and infusion preparations, and can be therapeutically applied by the topical, oral, rectal, parenteral, and additional routes.

For topical (including ophthalmic) sterile solutions, the compound of formula (I) together with conventional excipients in usual amounts are employed, such as for example sodium chloride and double-distilled water q.s., according to conventional procedure, such as filtration, aseptic filling into ampoules, and if necessary autoclaving for sterility.

A) Preparation of Indole-Derivatives

Example 1

Synthesis of Compound (121)

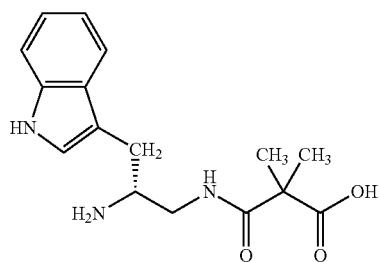

N-((R)-2-Amino-3-(1H-indol-3-yl)-propyl)-
2,2-dimethyl-malonamic acid

The Compound (121) was prepared according to the following steps:

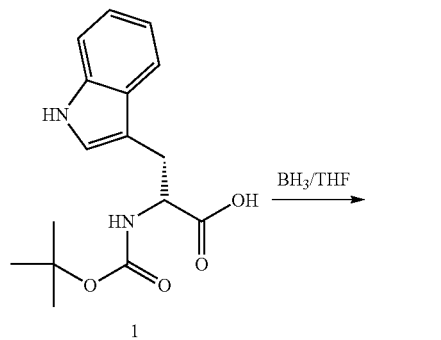

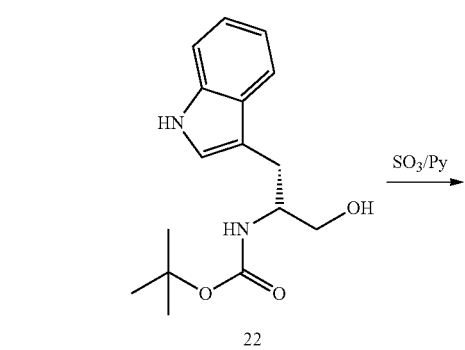

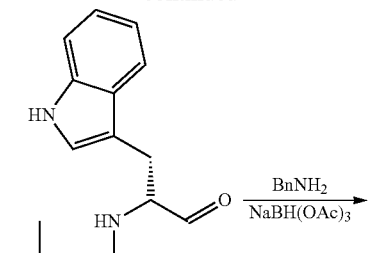

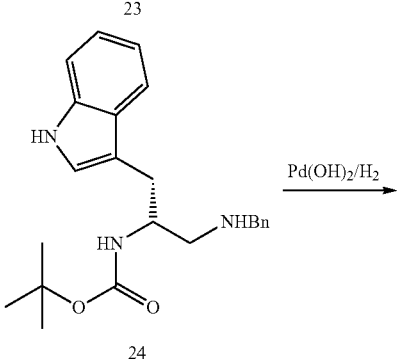

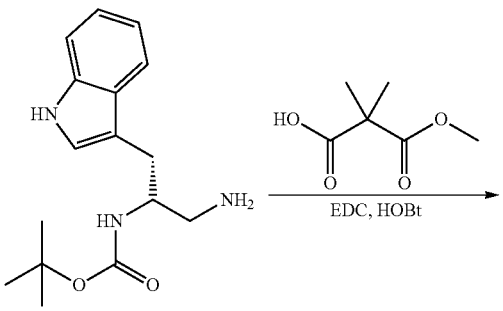

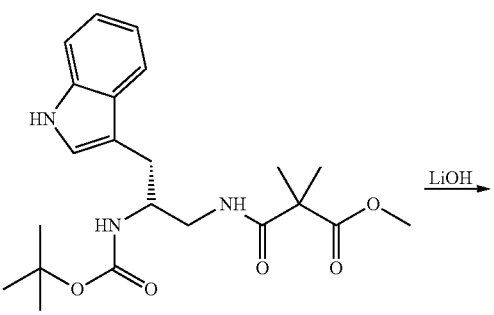

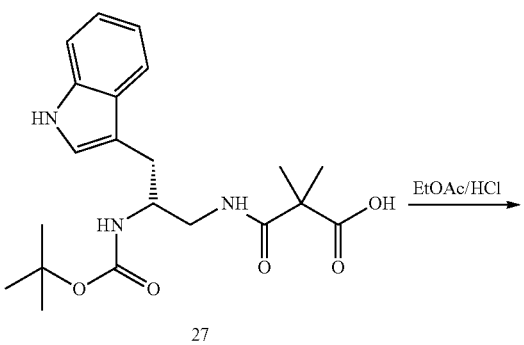

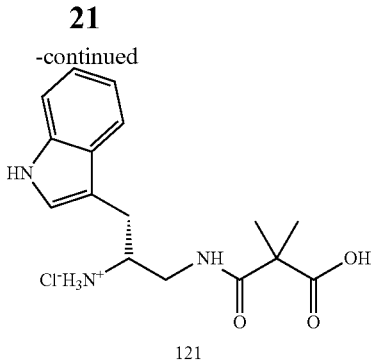

121 a) Compound 22

A solution of compound 1 (10.0 g, 33 mmol) and THF (50 mL) was cooled to 0° C. under $N_2$ atmosphere, then $BH_3$/THF was added dropwise. The temperature of the reaction mixture was allowed warm to room temperature. After stirring for 16 hours, the reaction mixture was quenched by $K_2CO_3$ (aq.), extracted with EtOAc (100 mL×3), the combined organic phase was washed with brine (50 mL) dried over $Na_2SO_4$, concentrated in vacuo and purified with column (PE/EtOAc=4:1) to give the product 22 as white solid (5.72 g, 60% yield). $^1$H NMR (400 MHz, $CDCl_3$): δ 1.46 (s, 9H), 3.02 (d, J=6.8 Hz, 2H), 3.80-3.55 (m, 2H), 4.10-3.95 (m, 1H), 4.86 (br s, 1H), 7.07 (s, 1H), 7.16 (t, J=7.2 Hz, 1H), 7.23 (t, J=7.2 Hz, 1H), 7.39 (d, J=8.4 Hz, 1H), 7.68 (d, J=7.6 Hz, 1H), 8.20 (s, 1H).

b) Compound 23

To a stirred solution of compound 22 (4.0 g, 14 mmol) in DCM (10 mL) was added DMSO (15 mL) and $Et_3N$ (3.23 g, 32 mmol). The mixture was cooled to 0° C., and then a solution of $SO_3$.Py (4.83 g, 30 mmol) in DMSO (15 mL) was added dropwise under $N_2$ atmosphere. After stirring for 1 hour at room temperature, the mixture was poured into ice/water (20 mL), and extracted with EtOAc (100 mL×3), the combined organic phase was washed with brine (50 mL), dried over $Na_2SO_4$ and concentrated in vacuo to give the crude product without purification (2.86 g, 71% yield). $^1$H NMR (400 MHz, DMSO-$d_6$): δ 1.37 (s, 9H), 3.02-2.85 (m, 1H), 3.20-3.12 (m, 1H), 4.14-4.05 (m, 1H), 4.20-4.06 (m, 1H), 7.00 (t, J=7.4 Hz, 1H), 7.08 (t, J=7.4 Hz, 1H), 7.17 (s, 1H), 7.54 (d, J=7.6 Hz, 1H), 7.52 (d, J=7.6 Hz, 1H), 9.55 (s, 1H), 10.88 (s, 1H).

c) Compound 24

To a stirred solution of compound 23 (500 mg, 1.7 mmol) in DCM (25 mL) was added $BnNH_2$ (214 mg, 2.0 mmol) and $NaBH(OAc)_3$ (1.1 g, 5.2 mmol). After stirring for 16 hours at room temperature, the mixture was poured into ice/water (20 mL) and extracted with DCM/MeOH (10:1, 20 mL×3). The combined organic phase was washed with brine (50 mL), dried over $Na_2SO_4$ and concentrated in vacuo. The residue was purified with Prep-TLC (DCM/MeOH=20/1) to give the product 24 as white solid (370 mg, 56% yield).

d) Compound 25

To a stirred solution of compound 24 (150 mg, 0.4 mmol) in MeOH (10 mL) was added $Pd(OH)_2$ (50 mg) and HOAc (catalyst). After stirring for 16 hours at room temperature under $H_2$ atmosphere, the mixture was poured into water (50 mL) and extracted with DCM/MeOH (10:1, 20 mL×3), the combined organic phase was washed with brine (50 mL), dried over $Na_2SO_4$ and concentrated in vacuo, the residue was purified with Prep-TLC (DCM/MeOH=30/1) to give the product 25 as white solid (83 mg, 70% yield). $^1$H NMR (400 MHz, DMSO-$d_6$): δ 1.37 (s, 9H), 3.02-2.85 (m, 1H), 3.20-3.12 (m, 1H), 4.14-4.05 (m, 1H), 4.20-4.06 (m, 1H), 7.00 (t, J=7.4 Hz, 1H), 7.08 (t, J=7.4 Hz, 1H), 7.17 (s, 1H), 7.54 (d, J=7.6 Hz, 1H), 7.52 (d, J=7.6 Hz, 1H), 9.55 (s, 1H), 10.79 (s, 1H).

e) Compound 26

To a stirred solution of compound 25 (350 mg, 1.20 mmol) in DMF (10 mL) was added 2-(methoxycarbonyl)-2-methylpropanoic acid (256 mg, 1.6 mmol), HOBt (243 mg, 1.8 mmol), EDC (607 mg, 2.5 mmol) and DIEA (774 mg, 6.0 mmol). After stirring for 16 hours at room temperature under $N_2$ atmosphere, the mixture was poured into water (50 mL) and extracted with EtOAc (20 mL×3). The organic phase was washed with brine (50 mL), dried over $Na_2SO_4$, concentrated in vacuo and the residue purified with Prep-TLC (DCM/MeOH=30/1) to give the product 26 as white solid (338 mg, 67% yield).

f) Compound 27

To a stirred solution of compound 26 (417 mg, 1 mmol) in MeOH/$H_2O$ (5:2. 7 mL) was added LiOH.$H_2O$ (168 mg, 4 mmol), After stirring for 4 hours at room temperature, HCl (con.) was added to the mixture to make PH to 5, extracted with EtOAc (20 mL×3), The combined organic phase was washed with brine (50 mL), dried over $Na_2SO_4$ and concentrated in vacuo to give the product 27 as white solid (256 mg, 81% yield).

g) Compound 121

A solution of compound 27 (200 mg, 0.500 mmol) in EtOAc/HCl (20 mL, 4 M) was stirred for 2 hours at room temperature, then concentrated in vacuo to give the product 121 as white solid (136 mg, 80% yield). $^1$H NMR (400 MHz, DMSO-$d_6$): δ 1.32 (s, 6H), 3.20-2.85 (m, 2H), 3.50-3.25 (m, 3H), 7.02 (t, J=7.2 Hz, 1H), 7.11 (t, J=7.2 Hz, 1H), 7.28 (s, 1H), 7.38 (d, J=7.6 Hz, 1H), 7.59 (d, J=7.6 Hz, 1H), 9.50-7.90 (m, 4H), 11.04 (s, 1H). LCMS [mobile phase: from 95% water (0.02% $NH_4Ac$) and 5% $CH_3CN$ to 40% water (0.02% $NH_4Ac$) and 60% $CH_3CN$ in 6 min, finally under these conditions for 0.5 min.] purity is 98.3%, Rt=2.974 min; MS Calcd.: 303.1; MS Found: 304.1 ([M+1]$^+$).

Example 2

Synthesis of Compound (171)

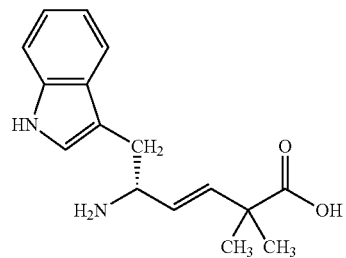

(E)-(R)-5-Amino-6-(1H-indol-3-yl)-
2,2-dimethyl-hex-3-enoic-acid (171)

The Compound (171) was prepared according to the following steps:

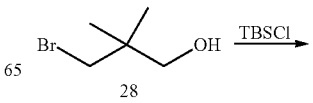

28

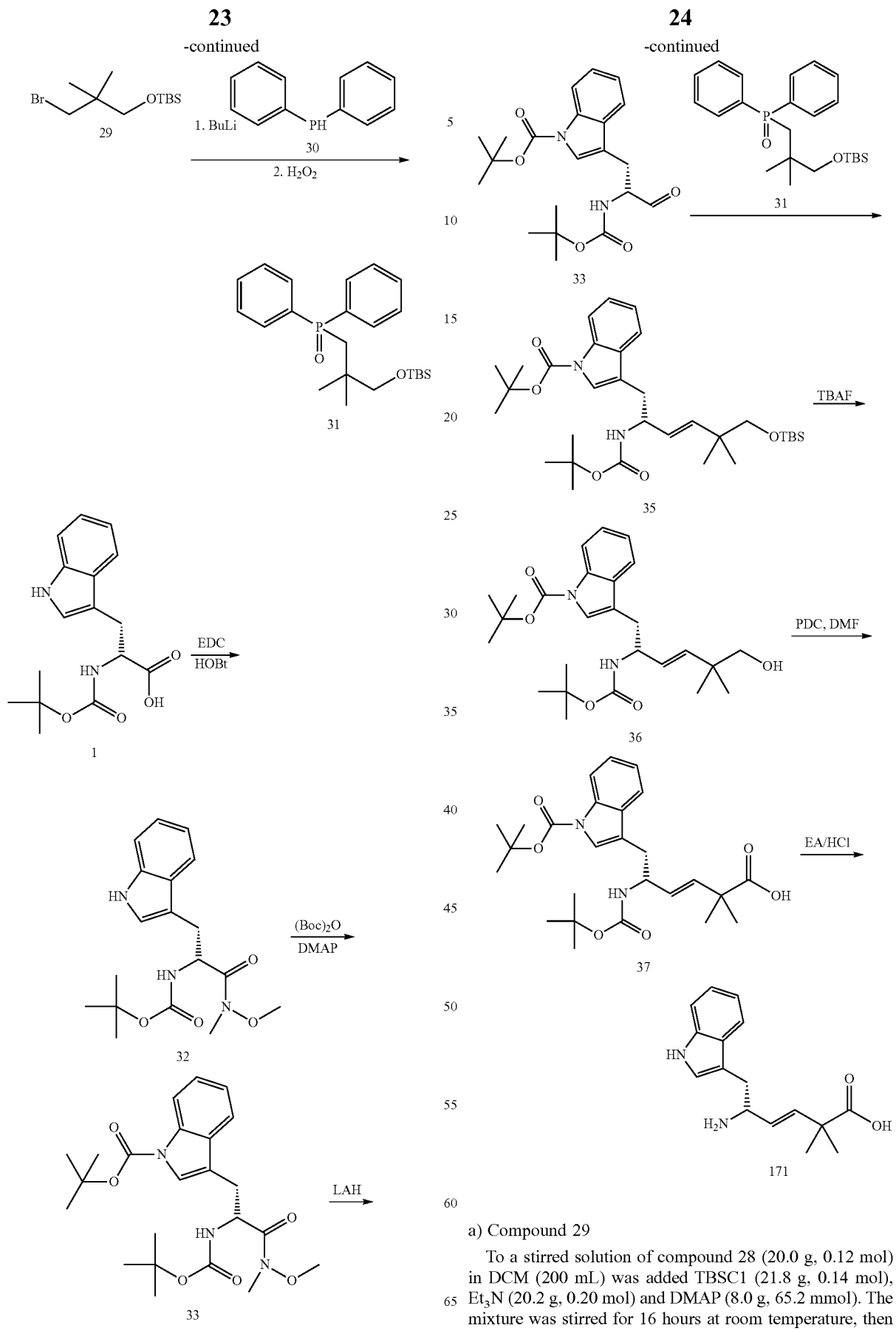
a) Compound 29
To a stirred solution of compound 28 (20.0 g, 0.12 mol) in DCM (200 mL) was added TBSCl (21.8 g, 0.14 mol), Et₃N (20.2 g, 0.20 mol) and DMAP (8.0 g, 65.2 mmol). The mixture was stirred for 16 hours at room temperature, then concentrated in vacuo and purified with column (PE) to give the product (32.0 g, 95% yield). $^1$H NMR (400 MHz, DMSO-d$_6$): δ 0.08 (s, 6H), 0.92 (s, 9H), 1.00 (s, 6H), 3.40 (s, 4H)

b) Compound 31

A solution of compound 30 (3.31 g, 17.8 mmol) in THF (10 mL) was cooled to −78° C., then BuLi (2.5M in hexane, 9.3 mL, 23.1 mmol) was added dropwise. After stirring for 1 hour at the same temperature, then compound 29 (4.98 g, 17.8 mmol) was added dropwise at −78° C. The reaction mixture was allowed to warm to room temperature. After stirring for 3 hours, the reaction mixture was quenched with NH$_4$Cl (sat., 20 mL), extracted with EtOAc (200 mL). The organic phase was washed with brine (50 mL), dried over Na$_2$SO$_4$ and concentrated in vacuo and the residue was purified with column (PE:EtOAc=4:1) to give the product 31 (4.20 g, 60% yield). $^1$H NMR (400 MHz, DMSO-d$_6$): δ 0.03 (s, 6H), 0.92 (s, 9H), 1.04 (s, 6H), 2.44 (d, J=10.8 Hz, 2H), 3.31 (s, 2H), 7.50-7.45 (m, 6H), 7.86-7.70 (m, 4H).

c) Compound 32

To a stirred solution of compound 1 (3.04 g, 10.0 mmol) in DMF (20 mL) was added N-Methoxy-N-methylamine Hydrochloride (1.95 g, 20.0 mmol), HOBt (1.35 g, 10.0 mmol), EDC (2.90 g, 15.0 mmol) and DIEA (774 mg, 6.0 mmol). After stirring for 16 hours at room temperature under N$_2$ atmosphere, the mixture was poured into H$_2$O (100 mL) and was extracted with EtOAc (40 mL×3). The combined organic phase was washed with brine (50 mL) dried over Na$_2$SO$_4$ and concentrated in vacuo and the residue was purified with column (PE:EtOAc=6:1) to give the product 32 as white solid (3.06 g, 88% yield).

d) Compound 33

To a stirred solution of compound 32 (6.50 g, 18.7 mmol) in DCM (100 mL) was added Boc$_2$O (8.20 g, 37.4 mmol), DMAP (1 g, 8.2 mmol) and DIEA (2.58 g, 20 mmol). After stirring for 16 hours at room temperature under N$_2$ atmosphere, the mixture was poured into H$_2$O (100 mL) and was extracted with EtOAc (100 mL×3), washed with brine (100 mL), dried over Na$_2$SO$_4$ and concentrated in vacuo and the residue was purified with column (PE: EtOAc=10:1) to give the product 33 (7.30 g, 87% yield). $^1$H NMR (400 MHz, DMSO-d$_6$): δ 1.43 (s, 9H), 1.70 (s, 9H), 3.20-3.01 (m, 5H), 3.73 (s, 1H), 5.40-5.00 (m, 1H), 7.35-7.20 (m, 2H), 7.46 (s, 1H), 7.56 (d, J=7.2 Hz, 1H), 8.14 (br s, 1H)

e) Compound 34

A mixture of LAH (111 mg, 2.9 mmol) in THF (10 mL) was cooled to −78° C., then a solution of compound 33 (1.0 g, 2.2 mmol) in THF (10 mL) was added dropwise slowly. After stirring for 2 hours at 0° C., the reaction mixture was quenched by KHSO$_4$ (sat.) and extracted with EtOAc (20 mL×3). The combined organic phase was washed with HCl (1N)(50 mL×2) and brine (50 mL), dried over Na$_2$SO$_4$ and concentrated in vacuo to give the crude product 34 (609 mg, 70% yield).

f) Compound 35

A solution of compound 31 (4.2 g, 10.3 mmol) in THF (50 mL) was cooled to −78° C., then BuLi (2.5 M in hexane, 4.5 mL, 11.3 mmol) was added dropwise and the mixture was stirred for 1 hour at the same temperature, then a solution of compound 34 (4.0 g, 10.3 mmol) in THF (10 mL) was added dropwise at −78° C. The reaction mixture was allowed to warm to room temperature. After stirring for 3 hours, the reaction mixture was quenched with NH$_4$Cl (sat., 20 mL), extracted with EtOAc (200 mL), the organic phase was washed with brine (50 mL), dried over Na$_2$SO$_4$, concentrated in vacuo and the residue was purified with column (PE: EtOAc=10:1) to give the product 35 (1.0 g, 17% yield). $^1$H NMR (400 MHz, DMSO-d$_6$): δ 0.01 (s, 6H), 0.93-0.85 (m, 15H), 1.28 (s, 9H), 1.68 (s, 9H), 3.00-2.90 (m, 2H), 3.27 (s, 1H), 4.61-4.50 (m, 2H), 5.39 (dd, J=15.6, 5.6 Hz, 1H), 5.57 (d, J=16.0 Hz, 1H), 7.36-7.20 (m, 2H), 7.41 (s, 1H), 7.57 (d, J=7.6 Hz, 1H), 8.20-8.10 (m, 1H).

g) Compound 36

To a solution of compound 35 (1 g, 1.8 mmol) in THF (10 mL) was added TBAF (913 mg, 3.49 mmol), After stirring for 3 hours at room temperature, the mixture was poured into water (50 mL) and extracted with EA (50 mL×3), the combined organic phase was washed with brine (50 mL), dried over Na$_2$SO$_4$, concentrated in vacuo and the residue was purified with column (PE: EtOAc=4:1) to give the product 36 (721 mg, 90% yield).

h) Compound 37

To a solution of compound 36 (459 mg, 1.00 mmol) in DMF (10 mL) was added PDC (1.90 g, 5.00 mmol). After stirring for 24 hours at room temperature, the mixture was poured into water (50 mL) and extracted with EtOAc (50 mL×3), the combined organic phase was washed with brine (50 mL), dried over Na$_2$SO$_4$, concentrated in vacuo and the residue was purified with column (PE: EtOAc=8:1) to give the product 37 (396 mg, 86% yield). $^1$H NMR (400 MHz, DMSO-d$_6$): δ 1.12 (s, 3H), 1.18 (s, 3H), 1.32 (s, 9H), 1.62 (s, 9H), 2.80-2.70 (m, 2H), 4.28-4.15 (m, 2H), 5.61 (dd, J=15.6, 6.0 Hz, 1H), 5.65 (d, J=16.0 Hz, 1H), 7.01 (d, J=8.0 Hz, 1H), 7.33-7.20 (m, 2H), 7.43 (s, 1H), 7.63 (d, J=7.2 Hz, 1H), 8.04 (d, J=7.6 Hz, 1H), 12.24 (br s, 1H).

i) Compound 171

A solution of compound 37 (236 mg, 0.5 mmol) in EtOAc/HCl (10 mL, 4 M) was stirred for 2 hours at room temperature, then concentrated in vacuo and purified by Prep-HPLC to give the TFA salt of product 171 as white solid (201 mg, 75% yield). $^1$H NMR (400 MHz, DMSO-d$_6$): δ 1.03 (s, 3H), 1.14 (s, 3H) 3.25-2.85 (m, 2H), 4.5-3.85 (m, 1H), 5.48 (dd, J=16.0, 8.0 Hz, 1H), 5.80 (d, J=16.4 Hz, 1H), 7.18-6.99 (m, 3H), 7.37 (d, J=8.0 Hz, 1H), 7.54 (d, J=7.6 Hz, 1H), 8.20-7.90 (br s, 3H), 10.98 (s, 1H), 12.41 (br s, 1H). LCMS [mobile phase: from 95% water (0.02% NH$_4$Ac) and 5% CH$_3$CN to 40% water (0.02% NH$_4$Ac) and 60% CH$_3$CN in 6 min, finally under these conditions for 0.5 min.] purity is >95%, Rt=3.127 min; MS Calcd.: 272.1; MS Found: 273.1 ([M+1]$^+$).

Examples 3 and 4

Synthesis of Compounds (172) and (173)

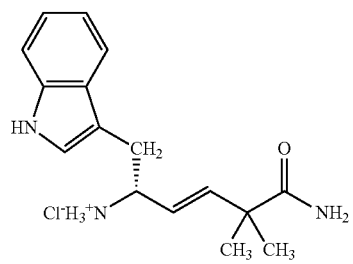

(172)

(E)-(R)-5-Amino-6-(1H-indol-3-yl)-
2,2-dimethyl-hex-3-enoic-acid amide

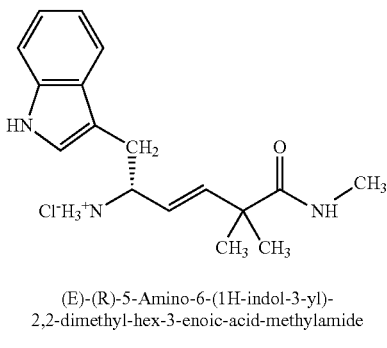

(E)-(R)-5-Amino-6-(1H-indol-3-yl)-
2,2-dimethyl-hex-3-enoic-acid-methylamide

The Compounds (172) and (173) was prepared according to the following steps:

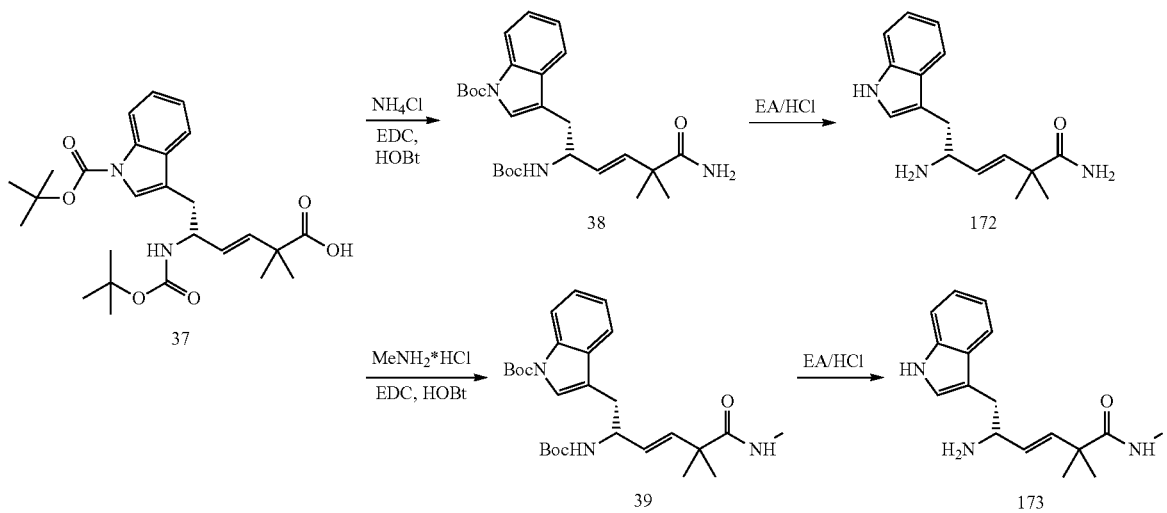

a) Compound 38

To a solution of compound 37 (100 mg, 0.20 mmol) in DMF (10 mL) was added NH$_4$Cl (54 mg, 1.0 mmol), HOBt (57 mg, 0.40 mmol), EDC (96 mg, 0.50 mmol) and DIEA (258 mg, 2.0 mmol). After stirring for 16 hours at room temperature under N$_2$ atmosphere, the mixture was poured into H$_2$O (50 mL) and extracted with EtOAc (20 mL×3). The combined organic phase was washed with brine (50 mL), dried over Na$_2$SO$_4$ and concentrated in vacuo, the residue was purified with Prep-TLC (PE/EtOAc=1/1) to give the product 38 as white solid (77 mg, 78% yield).

b) Compound 39

To a solution of compound 37 (100 mg, 0.20 mmol) in DMF (10 mL) was added methylamine hydrochloride salt (68 mg, 1.0 mmol), HOBt (57 mg, 0.40 mmol), EDC (96 mg, 0.50 mmol) and DIEA (258 mg, 2.0 mmol). After stirring for 16 hours at room temperature under N$_2$ atmosphere, the mixture was poured into H$_2$O (50 mL) and extracted with EtOAc (20 mL×3). The combined organic phase was washed with brine (50 mL), dried over Na$_2$SO$_4$ and con-centrated in vacuo, the residue was purified with Prep-TLC (PE/EtOAc=2/1) to give the product 39 as white solid (82 mg, 84% yield).

c) Compound 172

A solution of compound 38 (0.4 mmol) in EtOAc/HCl (10 mL, 4.0 M) was stirred for 2 hours at room temperature, the reaction mixture was concentrated in vacuo and the residue was purified by Prep-HPLC to give HCl salt of 172 (52 mg, 42% yield) as white solid. $^1$H NMR (400 MHz, DMSO-d$_6$): δ 1.00 (s, 3H), 1.10 (s, 3H), 3.20-2.95 (m, 2H), 3.90-3.42 (m, 1H), 5.51 (dd, J=15.6, 8.0 Hz, 1H), 5.79 (d, J=15.6 Hz, 1H), 6.76 (s, 1H), 6.90 (s, 1H), 7.20-6.99 (m, 3H), 7.36 (d, J=8.0 Hz, 1H), 7.57 (d, J=7.6 Hz, 1H), 8.20-7.95 (br s, 3H), 10.98 (s, 1H). LCMS [mobile phase: from 95% water (0.05% TFA) and 5% CH$_3$CN to 5% water (0.05% TFA) and 95% CH$_3$CN in 6 min, finally under these conditions for 0.5 min.] purity is >95%, Rt=2.552 min; MS Calcd.: 271.1; MS Found: 272.1 ([M+1]$^+$).

d) Compound 173

A solution of compound 39 (0.4 mmol) in EtOAc/HCl (10 mL, 4.0 M) was stirred for 2 hours at room temperature, the reaction mixture was concentrated in vacuo and the residue was purified by Prep-HPLC to give HCl salt of 172 (51 mg, 40% yield) as white solid. $^1$H NMR (400 MHz, DMSO-d$_6$): δ 1.00 (s, 3H), 1.10 (s, 3H) 2.51 (s, 3H), 3.20-2.90 (m, 2H), 3.95-3.80 (m, 1H), 5.51 (dd, J=15.6, 8.0 Hz, 1H), 5.74 (d, J=15.6 Hz, 1H), 7.20-6.99 (m, 4H), 7.36 (d, J=8.0 Hz, 1H), 7.57 (d, J=7.6 Hz, 1H), 8.25-8.10 (br s, 3H), 11.00 (s, 1H). LCMS [mobile phase: from 95% water (0.05% TFA) and 5% CH$_3$CN to 5% water (0.05% TFA) and 95% CH$_3$CN in 6 min, finally under these conditions for 0.5 min.] purity is >95%, Rt=2.606 min; MS Calcd.: 285.1; MS Found: 286.1 ([M+1]$^+$).

Example 5

Synthesis of Compound (271)

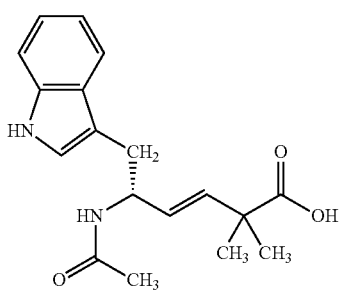

(E)-(R)-5-Acetylamino-6-(1H-indol-3-yl)-2,2-dimethyl-hex-3-enoic-acid

The Compound (271) was prepared according to the following steps:

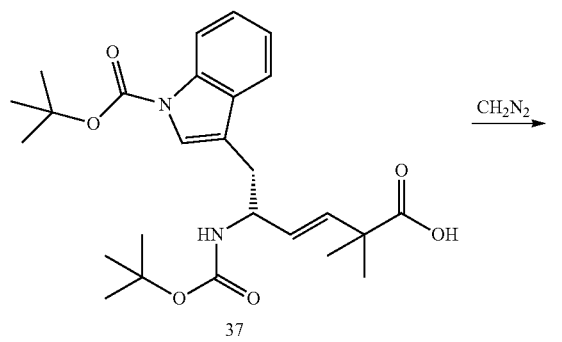

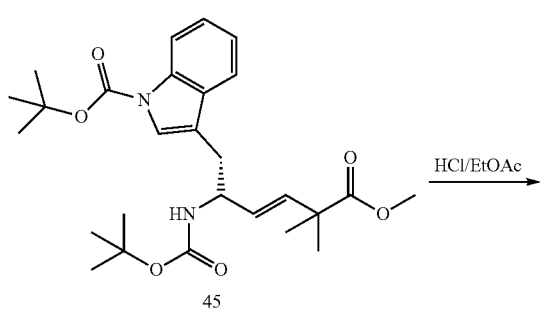

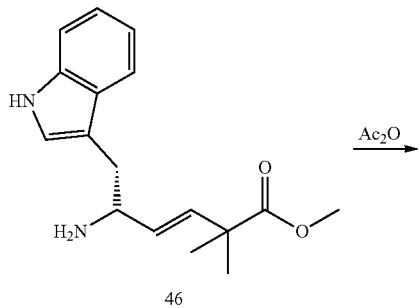

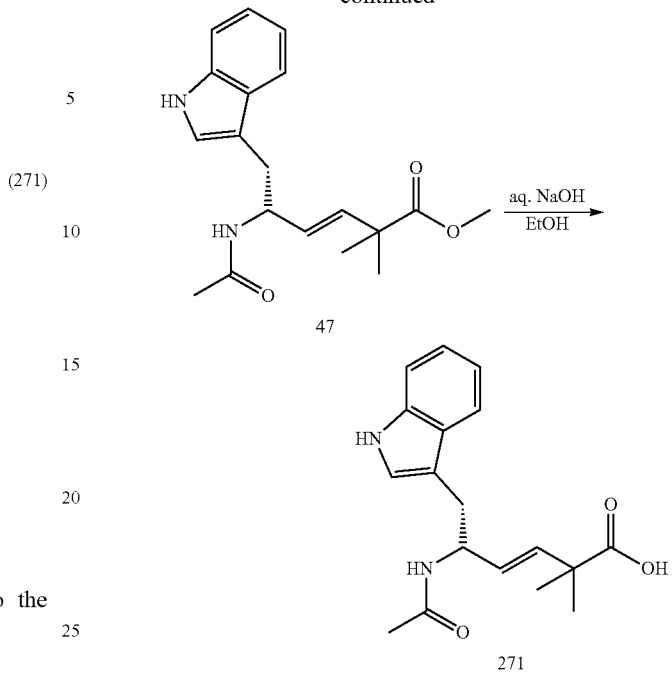

a) Compound 45

To a stirred solution of compound 37 (2.5 g, 5.3 mmol) in DCM (20 mL) was added a solution of diazomethane in Et$_2$O (53 mmol). After stirring for 12 h at room temperature, the mixture was concentrated in vacuo to give 45 (2.37 g, 92% yield), which was used without purification in next step.

b) Compound 46

A stirred solution of compound 45 (250 mg, 0.514 mmol) in HCl/EtOAc (10 ml, 2.9 M) was stirred for 2 h at room temperature. The solvent was removed in vacuo to give crude 46 (147 mg, 100% yield), which was used without purification in next step.

1H NMR (400 MHz, CDCl$_3$) □□ 1.26 (d, J=14.4 Hz, 6H), 1.95 (s, 3H), 3.00-3.11 (m, 2H), 3.66 (s, 3H), 4.88-4.91 (m, 1H), 5.51-5.57 (m, 2H), 5.71-5.75 (d, J=16.4 Hz, 1H), 7.02 (s, 1H), 7.13-7.23 (m, 2H), 7.37-7.39 (d, J=8.4 Hz, 1H), 7.61-7.63 (d, J=7.6 Hz, 1H), 8.28 (s, 1H).

c) Compound 47

To a stirred solution of compound 46 (147 mg, 0.514 mmol) and Et$_3$N (79 mg, 0.771 mmol) in THF (5 ml) was added Ac$_2$O (308 mg, 2.57 mmol) at ice-water cooled under N$_2$ atmosphere. The mixture was warmed to room temperature and stirred for over night. The mixture was distilled with DCM (15 mL), washed with saturated NaHCO$_3$ aq (3 ml×2) and brine (5 ml). The combined organic layer was dried over Na$_2$SO$_4$ and concentrated to give the crude product which was purified by prepare Prep-TLC (DCM: MeOH=20:1) to afford the desired product 47 (150 mg, 89% yield).

d) Compound 271

To a stirred solution of compound 47 (150 mg, 0.457 mmol) in EtOH (4 ml) was added 4 N NaOH (1.4 mL). After stirring for 2 h at room temperature, the reaction mixture was adjusted to pH=5.0 with HCl (2 N) and diluted with DCM (40 mL), The organic phase was separated out, and the aqueous layer was extracted with DCM/MeOH (10:1, 20 ml×2). The combined organic layer was dried over Na$_2$SO$_4$ and concentrated to give the crude product which was purified by prepare TLC (DCM: MeOH=10:1) to afford the desired product 271 (110 mg, 76% yield) as white solid.

$^1$H NMR (400 MHz, DMSO-d$_6$) ☐☐ 1.09 (s, 3H), 1.14 (s, 3H), 1.80 (s, 3H), 3.66 (s, 3H), 2.82-2.85 (m, 2H), 4.50-4.53 (m, 1H), 6.95-6.99 (m, 1H), 7.04-7.07 (m, 2H), 7.32-7.34 (d, J=8 Hz, 1H), 7.53-7.55 (d, J=7.6 Hz, 1H), 7.92-7.94 (d, J=8.4 Hz, 1H), 10.79 (s, 1H), 12.22 (s, 1H). LCMS (mobile phase: from 95% water (0.02% NH4Ac) and 10% CH$_3$CN to 40% water (0.02% NH4Ac) and 60% CH$_3$CN in 6 min, finally under these conditions for 0.5 min.) purity is >95%, Rt=2.687 min, MS Calcd.: 314.1; MS Found: 315.2 (M$^+$+H).

Examples 6 to 14

The following indole derivatives (E6 to E14) and (E 14a to E 14j) can be prepared in analogy to the examples 1 to 5 by using appropriate starting materials.

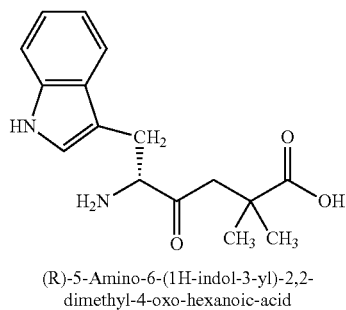

(R)-5-Amino-6-(1H-indol-3-yl)-2,2-dimethyl-4-oxo-hexanoic-acid (E6)

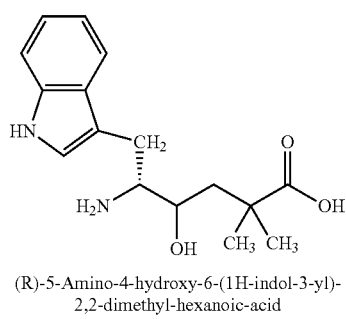

(R)-5-Amino-4-hydroxy-6-(1H-indol-3-yl)-2,2-dimethyl-hexanoic-acid (E7)

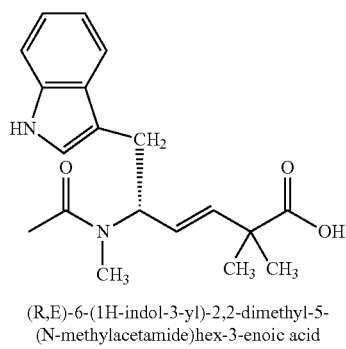

(R,E)-6-(1H-indol-3-yl)-2,2-dimethyl-5-(N-methylacetamide)hex-3-enoic acid (E8)

-continued

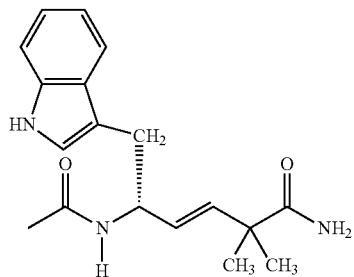

(E)-(R)-5-Acetylamino-6-(1H-indol-3-yl)-2,2-dimethyl-hex-3-enoic-acid-amide (E9)

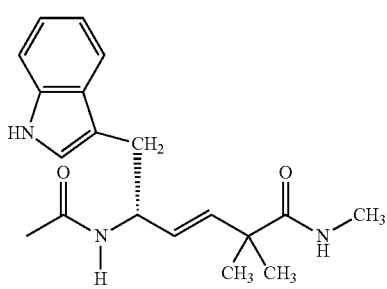

(E)-(R)-5-Acetylamino-6-(1H-indol-3-yl)-2,2-dimethyl-hex-3-enoic-acid-methylamide (E10)

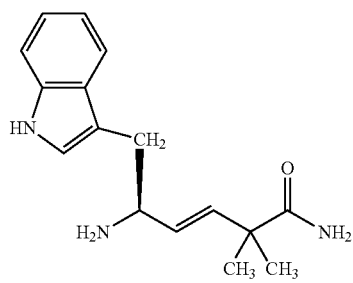

(E)-(S)-5-Amino-6-(1H-indol-3-yl)-2,2-dimethyl-hex-3-enoic-acid-amide (E11)

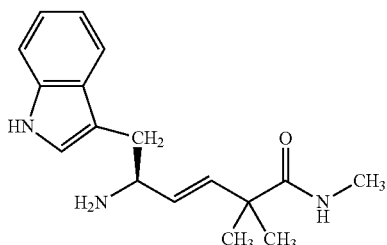

(E)-(S)-5-Amino-6-(1H-indol-3-yl)-2,2-dimethyl-hex-3-enoic-acid-methylamide (E12)

-continued

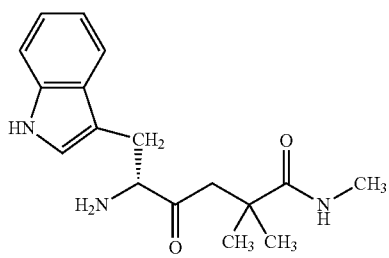

(R)-5-Amino-6-(1H-indol-3-yl)-
2,2-dimethyl-4-oxo-hexanoic-acid-methylamide (E13)

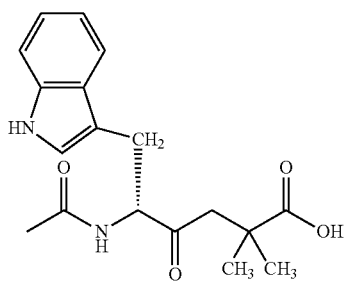

(R)-5-Acetylamino-6-(1H-indol-3-yl)-
2,2-dimethyl-4-oxo-hexanoic acid (E14)

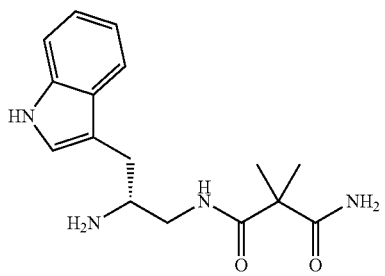

(R)-N1-(2-amino-3-(1H-indol-3-yl)
propyl)-2,2-dimethylmalonamide
$C_{16}H_{22}N_4O_2$ (E 14a)

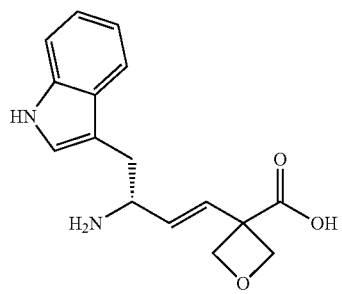

(R,E)-3-(3-amino-4-(1H-indol-3-yl)
but-1-en-1-yl)oxetane-3-carboxylic acid
$C_{16}H_{18}N_2O_3$ (E 14b)

-continued

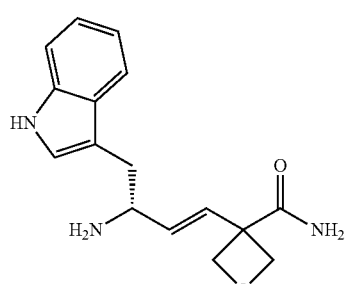

(R,E)-3-(3-amino-4-(1H-indol-3-yl)
but-1-en-1-yl)oxetane-3-carboxyamide
$C_{16}H_{19}N_3O_2$ (E 14c)

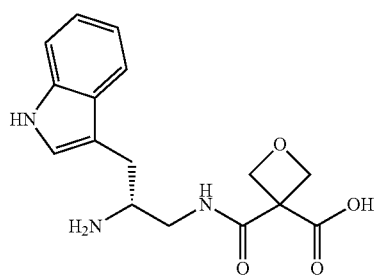

(R)-3-((2-amino-3-(1H-indol-3-yl)
propyl)carbamoyl)oxetane-3-carboxylic acid
$C_{16}H_{19}N_3O_4$ (E 14d)

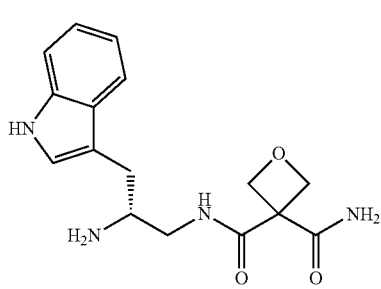

(R)-N-(2-amino-3-(1H-indol-3-yl)
propyl)oxetane-3,3-dicarboxamide
$C_{16}H_{20}N_4O_3$ (E 14e)

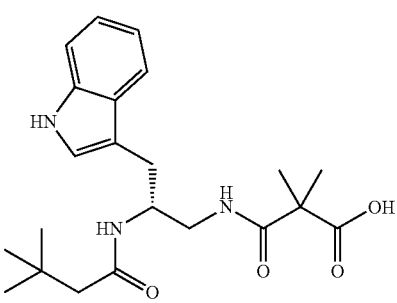

(R)-3-((2-(3,3-dimethylbutanamido)-3-
(1H-indol-3-yl)propyl)amino-2,2-
dimethyl-3-oxopropanoic acid
$C_{22}H_{31}N_3O_4$ (E 14f)

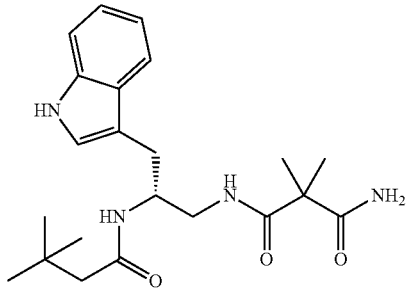

(R)-N1-(2-(3,3-dimethylbutanamido)-
3-(1H-indol-3-yl)propyl)-2,2-
dimethylmalonamide
$C_{22}H_{32}N_4O_3$

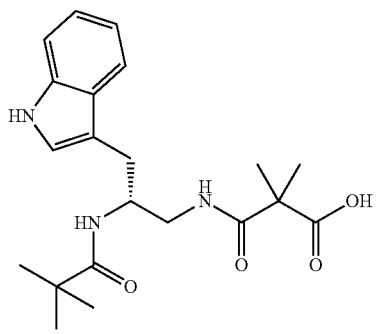

(R)-3-((3-(1H-indol-3-yl)-2-
pivalamidopropyl)amino)-
2,2-dimethyl-3-oxopropanoic acid
$C_{21}H_{29}N_3O_4$

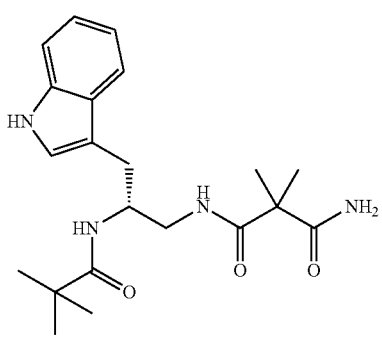

(R)-N1-(3-(1H-indol-3-yl)-2-
pivalamidopropyl)-2,2-
dimethylmalonamide
$C_{21}H_{30}N_4O_3$

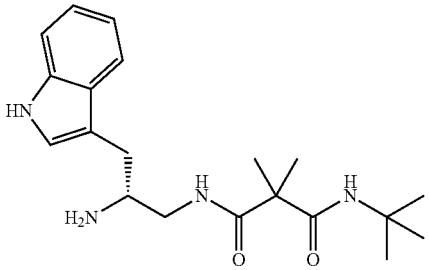

(R)-N1-(2-amino-3-(1H-indol-3-yl)
propyl)-N3-(tert-butyl)-2,2-
dimethylmalonamide
$C_{20}H_{30}N_4O_2$ B) Formulation Examples The following examples are given by way of illustration for compositions of compounds of formula (I). As active ingredient, the compound according to example 1 can be used in the following compositions.

Example 15

Tablet Formulation

A formulation for a tablet containing 10 milligrams of the active ingredient of example 1 is as follows:

|  | mg |
|---|---|
| Active Ingredient | 10 |
| Lactose | 61 |
| Microcrystalline Cellulose | 25 |
| Talcum | 2 |
| Magnesium stearate | 1 |
| Colloidal silicon dioxide | 1 |

Example 16

Coated Tablet Formulation

Another suitable formulation for a tablet containing 100 mg of the compound of example 2 is as follows:

|  | mg |
|---|---|
| Active Ingredient | 100 |
| Polyvinylpyrrolidone crosslinked | 10 |
| Potato starch | 20 |
| Polyvinylpyrrolidone | 19 |
| Magnesium stearate | 1 |
| Microcrystalline Cellulose | 50 |
| Film coated and colored. | |
| The film coating material consists of: | |
| Hypromellose | 10 |
| Microcryst. Cellulose | 5 |
| Talcum | 5 |
| Polyethylene glycol | 2 |
| Color pigments | 5 |

Example 17

Capsule Formulation

A suitable formulation for a capsule containing 50 milligrams of the active ingredient of example 1 is as follows:

|  | mg |
| --- | --- |
| Active Ingredient | 50 |
| Corn starch | 26 |
| Dibasic calcium phosphate | 50 |
| Talcum | 2 |
| Colloidal silicon dioxide | 2 |

This formulation is filled in a gelatin capsule.

Example 18

Solution for Injection

A suitable formulation for an injectable solution is as follows:

| Active Ingredient | mg | 10 |
| --- | --- | --- |
| Sodium chloride | mg | q.s. |
| Water for Injection | mL | ad 1.0 |

Example 19

Liquid Formulation

A suitable formulation for 1 liter of an ophthalmic solution containing 2 milligrams of active ingredient in one milliliter of the mixture is as follows:

|  | mg |
| --- | --- |
| Active Ingredient | 2 |
| Sorbitol | 150 |
| Buffering agent | q.s. |
| Colorant | q.s. |
| Purified water | Ad 1000 ml |

Example 20

Ophthalmic Formulation 100 g of the solution contain:

|  | g |
| --- | --- |
| Active Ingredient | 0.1 |
| Hydroxyethylcellulose | 0.4 |
| Sodium cloride | q.s. |
| Purified water | ad 100 g |

Example 21

Suspension Formulation 1.0 g of the suspension contains the following:

|  | g |
| --- | --- |
| Active Ingredient | 0.10 |
| Hypromellose | 0.01 |
| Purified water | Ad 1.0 g |

Hypromellose is dispersed in water homogeneously with a high speed mixer/blender. After about one hour of hydration time of the hypromellose, the active ingredient is blended homogeneously into the hypromellose solution. The viscosity of the suspension can be adjusted by the amount of hypromellose, resulting in a very stable suspension with a very slow tendency of particle sedimentation and particle agglomeration.

Example 22

Solution for Injection 1.0 ml of solution contain:

|  | g |
| --- | --- |
| Active Ingredient | 0.05 |
| Mannitol | q.s. |
| DMSO | 0.10 |
| Water for injection | Ad 1.0 ml |

The active ingredient is dissolved in DMSO by stirring and heating (solution 1). The mannitol is dissolved in WFI (solution 2). After cooling down to room temperature solution 1 is mixed with solution 2 by continuous stirring. The solution is sterilized by filtration of by autoclaving.

C) Pharmacology Tests

The compounds of formula (I) of the present invention and pharmaceutical compositions containing them are characterized by advantageous properties. The compounds and pharmaceutical compositions exhibit, in standard accepted reliable test procedures, the following valuable properties and characteristics:

Pharmacological Testing Model 1

In an experimental model of glaucoma, there is increased expression of amyloid precursor protein (APP) and likely related apoptosis in retinal ganglion cells (RGC) [McKinnon, S. J., "Caspase activation and amyloid precursor protein cleavage in rat ocular hypertension", Invest Ophthalmol Vis Sci. 2002 April; 43(4):1077-87]. Furthermore, injection of $A\beta_{1-42}$ induces apoptosis in RGC. Interference with APP-Aβ pathway such as inravitreal application of antibody, inhibition of β-secretase activity or oligomerisation inhibition prevents, at least temporally (depending on the treatment) RGC apoptosis in glaucoma resulting from increased ocular pressure (Guo, et al., 2007). Therefore, it can be concluded that substances of formula (I), which exhibit a dual mechanism of action, i.E., β-sheet breaking activity and oligomerisation inhibition, show a neuroprotective activity.

In the male Dark Agouti rat model, glaucoma is produced by injection of 50 µl of hypertonic saline into episcleral vein of one eye to induce increased ocular pressure (chronic ocular hypertension—OHT), while the opposite eye serves as a control [Morrison J. C., "A rat model of chronic pressure-induced optic nerve damage", Exp Eye Res. 1997; 64(1): 85-96]. In treatment groups (N=4-6 per group), various doses of substances of the present invention are injected intravitreally (in 5 μl volume) shortly before the glaucoma induction. The extent of RGC apoptosis at 3 weeks and 6 weeks after chronic ocular hypertension (OHT) induction is assessed in each animal by dynamic confocal scanning laser ophthalmoscopy and fluorescent-labeled Annexin V.

Animals are sacrificed after 6 weeks and their eyes are enucleated and fixed in 4% paraformaldehyde overnight. Afterwards, retinas are separated for assessing apoptosis related changes, for example: as visualized with FITC Annexin V kit (BD Biosciences, Franklin Lakes, USA) [Cordeiro, M. F. 2004 "Real-time imaging of single nerve cell apoptosis in retinal neurodegeneration", Proc Natl Acad Sci USA, 101, 13352-6; Kietselaer, B. L., 2003, "The role of labeled Annexin AS in imaging of programmed cell death. Form animal to clinical imaging", Q J Nucl Med, 47, 349-61], or TUNEL (dUTP nick end labeling) [Roche, In situ cell death detection kit, fluorescein labeled] [Szydlowsky K., Kaminska B., 2007, "Neuroprotective activity of selective mGlu1 and mGlu5 antagonists in vitro and in vivo", Eur. J. Pharmacol. 554, 18-29]. In animals treated with experimental substances of the instant invention, there is a decrease in RGC apoptosis at the dose of 0.1 mg/ml least at one time point assessed.

Pharmacological Testing Model 2

In further experiments, rats are treated systemically (s.c.) and the experiments are repeated as above. The aim of this study is to verify whether systemic administration of a compound of formula (I) producing eye concentrations similar to those after intravitreal application also provides neuroprotective effect against IOP-induced apoptosis. In animals treated systemically with the substances, there is a dose dependent decrease in RGC apoptosis reaching significance at the dose of 240 mg/kg (mesylate) and observed at 6 weeks post glaucoma induction.

Pharmacological Testing Model 3

Additionally, effects of the compounds of formula (I) to monomeric $A\beta_{1-42}$ can be determined by surface plasmon resonance (SPR).

Materials and Methods

Preparation of Aβ

$A\beta_{1-42}$ (#60-0-80, American Peptide, Sunnyvale, Calif. USA) was dissolved to 1 mg/ml in Hexafluoroisopropanol (HFIP). The tube was tightly sealed and incubated at room temperature for 1.5 h while shaking. 100 μg aliquots were prepared in low binding eppendorf tubes and frozen at −80° C. for 30-60 minutes. After lyophilization over night the aliquots were stored at −20° C. until use. One HFIP treated Aβ aliquot was thawed and freshly dissolved in DMSO (anhydrous) and this 5 mM stock solution was diluted to 100 μM in 10 mM sodium acetate (pH4.0) immediately before immobilization.

Surface Plasmon Resonance (SPR)

SPR studies were performed using a Biacore X100 biosensor instrument (GE Lifesciences, Uppsala, Sweden), equipped with two flow cells on a sensor chip. Aβ monomers were covalently coupled to one flow cell of CM7 sensor chips (GE Lifesciences, Uppsala, Sweden) via primary amines using the Amine Coupling Kit (GE Lifesciences, Uppsala, Sweden). As a control, ethanolamine was immobilized on the reference channel. 3 different chips were used and immobilization levels for Aβ were comparable (21605RU, 22180RU and 21929RU, respectively). One RU represents about 1 pg/mm² of the analytes on the surface matrix of the sensor chip.

Compounds were dissolved in DMSO and diluted further in DMSO to give 1000× concentrated stock solutions. Then they were diluted 1:1000 in HBS-EP buffer which contains 0.01M HEPES, pH7.4, 0.15M NaCl, 3 mM EDTA, and 0.005% of surfactant P20. HBS-EP containing 0.1% (v/v) DMSO was used as assay running buffer. Compounds were injected over the sensor chip in concentrations ranging from 0.1 nM to 300 nM at a flow rate of 10μl/min for 180 s at 25° C. Concentrations were tested in duplicate.

The RUs elicited by the compound injected into the ethanolamine control flow cell was set as reference response and subtracted from the RUs elicited by the same compound injected to the Aβ saturated flow cell. The relationships between each RU obtained at the steady state of binding (plateau of the binding curve) and each concentration of the compound were plotted.

After the analyte injection was stopped, HBS-EP buffer was flowed over the chip for 180 s to allow the bound analyte to dissociate from the immobilized Aβ and the dissociation curves were obtained. After the dissociation phase, regeneration solution (1M NaCl, 50 mM NaOH) was injected and flowed over the chip for 30 s to remove the residual bound analytes from the immobilized Aβ.

Biacore X100 control software Ver 1.1 was used to record the binding curves and Biacore X100 evaluation software Ver 1.1 to analyze them (plot each RU at the steady state vs. concentration of analyte, fit the plot, determine $K_D$ values). The dissociation equilibrium constant $K_D$ of the analyte to the immobilized Aβ was determined from the steady-state levels estimating the maximum RU $R_{max}$ and calculating the $K_D$ as the concentration of the compound that elicited one-half of the $R_{max}$.

By performing repeating tests, the following IC-50 values can be found for the example compounds:

| Compound | IC-50 (nM) |
| --- | --- |
| Example 1 | 2.8 +/− 1.5 |
| Example 2 | 1.4 +/− 1.0 |
| Example 3 | 0.5 +/− 0.3 |
| Example 4 | 6.8 +/− 3.2 |
| Example 5 | 42.1 +/− 0.7 |

These data show that the compounds of formula (I) of the instant invention are useful for the treatment of Alzheimer's Disease and for the treatment of ocular diseases, such as glaucoma.

Moreover, plausible synergistic therapeutic effects can be found from a combined treatment with compounds of formula (I) and either intraocular pressure lowering agents currently used in glaucoma or other drug compounds such as antioxidants, calcium channel blockers, NO synthase inhibitors, neurotrophins and antiapoptotic agents.

Further synergistic effects can be found from a combined administration of a compound of formula (I) (such as Example 1) and the drug compound memantine.

What is claimed is:

1. A method for treating glaucoma comprising the step of administering to a patient in need thereof a therapeutically effective amount of a compound of formula (I)

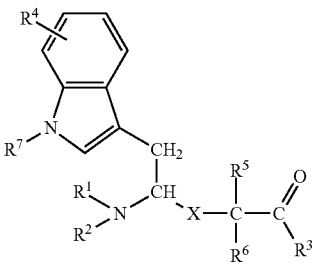

(I)

wherein:
R¹ is hydrogen, —$C_{1-6}$-alkyl, cyclo$C_{3-12}$-alkyl, —C(O)—R or —C(O)OR;
R² is hydrogen, —$C_{1-6}$-alkyl or cyclo$C_{3-12}$-alkyl;
R³ is —OR, —NHR or —NR₂;
R⁴ is hydrogen, halogen, cyano, trifluoromethyl, —$C_{1-6}$-alkyl, —$C_{6-10}$-aryl, heteroaryl, —OR, —NHR, —NRR, —C(O)—R or —C(O)—NHR;
R⁵ is hydrogen, —$C_{1-6}$-alkyl or $C_{2-6}$-alkenyl;
R⁶ is hydrogen, —$C_{1-6}$-alkyl or $C_{2-6}$-alkenyl; or
R⁵ and R⁶ together with the carbon atoms carrying them form a cyclic system with 3 to 6 carbon atoms;
R is hydrogen, —$C_{1-6}$-alkyl, or —$C_{6-10}$-aryl;
X is —C(O)CH₂—, —CH(OH)CH₂—, —CH=CH— or —CH₂—NH—C(O)—; and
R⁷ is hydrogen, methyl, ethyl, propyl or cyclopropyl;
or an optical isomer or a pharmaceutically acceptable salt thereof.

2. The method of claim 1, wherein:
R¹ is hydrogen, —$C_{1-6}$-alkyl, —C(O)—R or —C(O)OR;
R² is hydrogen, —$C_{1-6}$-alkyl or cyclo$C_{3-12}$-alkyl;
R³ is —OR, —NHR or —NR₂;
R⁴ is hydrogen, halogen, cyano, trifluoromethyl, or —$C_{1-6}$-alkyl;
R⁵ is —$C_{1-6}$-alkyl;
R⁶ is —$C_{1-6}$-alkyl; or
R⁵ and R⁶ together with the carbon atoms carrying them form a cyclic system with 3 to 6 carbon atoms;
R is hydrogen, —$C_{1-6}$-alkyl, or —$C_{6-10}$-aryl;
X is —C(O)CH₂—, —CH(OH)CH₂—, —CH=CH— or —CH₂—NH—C(O)—; and
R⁷ is hydrogen, methyl, ethyl, propyl or cyclopropyl.

3. The method of claim 1, wherein:
R¹ is hydrogen, —$C_{1-6}$-alkyl, —C(O)—R or —C(O)—OR;
R² is hydrogen or —$C_{1-6}$-alkyl;
R³ is —OR, —NHR or —NR₂;
R⁴ is hydrogen, halogen, cyano, trifluoromethyl, or —$C_{1-6}$-alkyl;
R⁵ is hydrogen or —$C_{1-6}$-alkyl;
R⁶ is hydrogen or —$C_{1-6}$-alkyl; or
R⁵ and R⁶ together with the carbon atom carrying them form a cyclic system with 3 to 6 carbon atoms
R is hydrogen or —$C_{1-6}$-alkyl;
X is —C(O)CH₂—, —CH(OH)CH₂—, —CH=CH— or —CH₂NHC(O)—; and
R⁷ is hydrogen or methyl.

4. The method of claim 1, wherein:
R¹ is hydrogen, —$C_{1-3}$-alkyl, or —C(O)—CH₃;
R² is hydrogen or —$C_{1-3}$-alkyl;
R³ is —OR, —NHR or —NR₂;
R⁴ is hydrogen or halogen;
R⁵ is —$C_{1-3}$-alkyl;
R⁶ is —$C_{1-3}$-alkyl;
R is hydrogen or —$C_{1-3}$-alkyl;
X is —C(O)CH₂—, —CH(OH)CH₂—, —CH=CH— or —CH₂NHC(O)—; and
R⁷ is hydrogen.

5. The method of claim 1, wherein:
R¹ is hydrogen, —$C_{1-3}$-alkyl, or —C(O)—CH₃;
R² is hydrogen;
R³ is —OR —NHR;
R⁴ is hydrogen;
R⁵ is hydrogen or —$C_{1-3}$-alkyl;
R⁶ is hydrogen or —$C_{1-3}$-alkyl;
R is hydrogen or —$C_{1-3}$-alkyl;
X is —C(O)CH₂—, —CH(OH)CH₂—, —CH=CH— or —CH₂NHC(O)—; and
R⁷ is hydrogen.

6. The method of claim 1, wherein:
R¹ is hydrogen or —C(O)—CH₃;
R² is hydrogen;
R³ is —OR —NHR;
R⁴ is hydrogen;
R⁵ is —$C_{1-3}$-alkyl;
R⁶ is —$C_{1-3}$-alkyl;
R is hydrogen or —$C_{1-3}$-alkyl;
X is —C(O)CH₂—, —CH(OH)CH₂—, —CH=CH— or —CH₂NHC(O)—; and
R⁷ is hydrogen.

7. The method of claim 1, wherein the group X is —C(O)CH₂— or —CH(OH)CH₂— or —CH=CH—.

8. The method of claim 1, wherein the chiral center carrying the amino group and the group X has R-configuration.

9. The method of claim 1, wherein said compound is selected from the group consisting of:
N—((R)-2-amino-3-(1H-indol-3-yl)-propyl)-2,2-dimethyl-malonamic acid,
(E)-(R)-5-amino-6-(1H-indol-3-yl)-2,2-dimethyl-hex-3-enoic-acid,
(E)-(R)-5-amino-6-(1H-indol-3-yl)-2,2-dimethyl-hex-3-enoic acid amide,
(E)-(R)-5-amino-6-(1H-indol-3-yl)-2,2-dimethyl-hex-3-enoic-acid-methylamide,
(E)-(R)-5-acetylamino-6-(1H-indol-3-yl)-2,2-dimethyl-hex-3-enoic-acid,
(R)-5-amino-6-(1H-indol-3-yl)-2,2-dimethyl-4-oxo-hexanoic-acid,
(R)-5-amino-4-hydroxy-6-(1H-indol-3-yl)-2,2-dimethyl-hexanoic-acid,
(R,E)-6-(1H-indol-3-yl)-2,2-dimethyl-5-(N-methylacetamide)hex-3-enoic acid,
(E)-(R)-5-acetylamino-6-(1H-indol-3-yl)-2,2-dimethyl-hex-3-enoic-acid-amide,
(E)-(R)-5-acetylamino-6-(1H-indol-3-yl)-2,2-dimethyl-hex-3-enoic-acid-methylamide,
(E)-(S)-5-amino-6-(1H-indol-3-yl)-2,2-dimethyl-hex-3-enoic-acid-amide,
(E)-(S)-5-amino-6-(1H-indol-3-yl)-2,2-dimethyl-hex-3-enoic-acid-methylamide,
(R)-5-amino-6-(1H-indol-3-yl)-2,2-dimethyl-4-oxo-hexanoic-acid-methylamide,
(R)-5-acetylamino-6-(1H-indol-3-yl)-2,2-dimethyl-4-oxo-hexanoic acid,
(R)-N1-(2-amino-3-(1H-indol-3-yl)propyl)-2,2-dimethylmalonamide,
(R,E)-3-(3-amino-4-(1H-indol-3-yl)but-1-en-1-yl)oxetane-3-carboxylic acid, (R,E)-3-(3-amino-4-(1H-indol-3-yl)but-1-en-1-yl)oxetane-3-carboxyamide,
(R)-3-((2-amino-3-(1H-indol-3-yl)propyl)carbamoyl)oxetane-3-carboxylic acid,
(R)-N-(2-amino-3-(1H-indol-3-yl)propyl)oxetane-3,3-dicarboxamide,
(R)-3-((2-(3,3-dimethylbutanamido)-3-(1H-indol-3-yl)propyl)amino-2,2-dimethyl-3-oxopropanoic acid,
(R)-N1-(2-(3,3-dimethylbutanamido)-3-(1H-indol-3-yl)propyl)-2,2-dimethylmalonamide,
(R)-3-((3-(1H-indol-3-yl)-2-pivalamidopropyl)amino)-2,2-dimethyl-3-oxopropanoic acid,
(R)-N1-(3-(1H-indol-3-yl)-2-pivalamidopropyl)-2,2-dimethylmalonamide,
(R)-N1-(2-amino-3-(1H-indol-3-yl)propyl)-N3-(tert-butyl)-2,2-dimethylmalonamide,
and pharmaceutically acceptable salts thereof.

* * * * *